(12) United States Patent
Beeckler et al.

(10) Patent No.: US 9,848,943 B2
(45) Date of Patent: Dec. 26, 2017

(54) ABLATION CATHETER WITH DEDICATED FLUID PATHS AND NEEDLE CENTERING INSERT

(71) Applicant: BIOSENSE WEBSTER (ISRAEL) LTD., Yokneam (IL)

(72) Inventors: Christopher Beeckler, Brea, CA (US); Athanassios Papaioannou, Los Angeles, CA (US); Rowan Hettel, Pasadena, CA (US); Maribeth Esguerra Wilczynski, Glendale, CA (US)

(73) Assignee: Biosense Webster (Israel) Ltd., Yokneam, IL (US)

( * ) Notice: Subject to any disclaimer, the term of this patent is extended or adjusted under 35 U.S.C. 154(b) by 795 days.

(21) Appl. No.: 14/256,876

(22) Filed: Apr. 18, 2014

(65) Prior Publication Data
US 2015/0297290 A1    Oct. 22, 2015

(51) Int. Cl.
*A61B 18/14*    (2006.01)
*A61B 18/00*    (2006.01)

(52) U.S. Cl.
CPC ...... *A61B 18/1477* (2013.01); *A61B 18/1492* (2013.01); *A61B 2018/00029* (2013.01);
(Continued)

(58) Field of Classification Search
CPC ............ A61B 18/1477; A61B 18/1492; A61B 2018/1475; A61B 2018/1472;
(Continued)

(56) References Cited

U.S. PATENT DOCUMENTS

RE34,502 E    1/1994   Webster, Jr.
5,336,222 A   8/1994   Durgin, Jr. et al.
(Continued)

FOREIGN PATENT DOCUMENTS

EP     1 205 156 A2    5/2002
WO    WO 94/10925      5/1994
(Continued)

OTHER PUBLICATIONS

Partial European Search Report dated Mar. 30, 2016 for EP Application No. 16150149.9, 6 pages.
(Continued)

*Primary Examiner* — Thomas Giuliani
(74) *Attorney, Agent, or Firm* — Lewis Roca Rothgerber Christie LLP

(57) ABSTRACT

An irrigated needle electrode ablation catheter has a distal tip section with a tip electrode, a needle electrode assembly longitudinal movable relative to the catheter, and a needle centering insert set in a channel in the tip electrode. The assembly has a proximal tubing and a distal needle electrode, and the insert supports the needle electrode in the channel at a predetermined separation distance from the tip electrode while enabling irrigation to flow circumferentially around the needle electrode through the channel and exit at the distal end of the tip electrode. The catheter also provides a first dedicated fluid pathway through the assembly and exits at the distal end of the needle electrode, and a second dedicated fluid pathway to supply fluid to the channel in the tip electrode, wherein the second pathway is defined by a guide tube and directed by a plunger member.

16 Claims, 19 Drawing Sheets

(52) U.S. Cl.
CPC ............ *A61B 2018/1425* (2013.01); *A61B 2018/1475* (2013.01); *A61B 2218/002* (2013.01)

(58) Field of Classification Search
CPC .... A61B 2018/1425; A61B 2018/1427; A61B 2018/00029; A61B 2218/002
USPC ........................................ 606/34, 41, 44, 48
See application file for complete search history.

(56) References Cited

U.S. PATENT DOCUMENTS

| | | |
|---|---|---|
| 5,391,199 A | 2/1995 | Ben-Haim |
| 5,403,311 A | 4/1995 | Abele et al. |
| 5,443,489 A | 8/1995 | Ben-Haim |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-haim |
| 5,897,529 A | 4/1999 | Ponzi |
| 6,123,699 A | 9/2000 | Webster, Jr. |
| 6,171,277 B1 | 1/2001 | Ponzi |
| 6,183,463 B1 | 2/2001 | Webster, Jr. |
| 6,575,931 B1 | 6/2003 | Ponzi |
| 6,623,474 B1 | 9/2003 | Ponzi |
| 8,287,531 B2 | 10/2012 | Mest |
| 2003/0006759 A1 | 1/2003 | Govari |
| 2004/0210284 A1 | 10/2004 | Okada |
| 2012/0150178 A1* | 6/2012 | Durgin ............... A61B 18/1492 606/46 |

FOREIGN PATENT DOCUMENTS

| | | |
|---|---|---|
| WO | WO 95/02995 | 2/1995 |
| WO | WO 96/05758 | 2/1996 |
| WO | WO 97/24983 | 7/1997 |
| WO | WO 98/29033 | 7/1998 |
| WO | WO 99/52459 | 10/1999 |
| WO | WO 2005/079901 A1 | 9/2005 |

OTHER PUBLICATIONS

European Extended Search Report dated Jul. 28, 2016 for EP Application No. 16150149.9, 11 pages.
European Patent Office Partial Search Report for EP Application No. 15164012.5, dated Sep. 14, 2015, 5 pages.

* cited by examiner

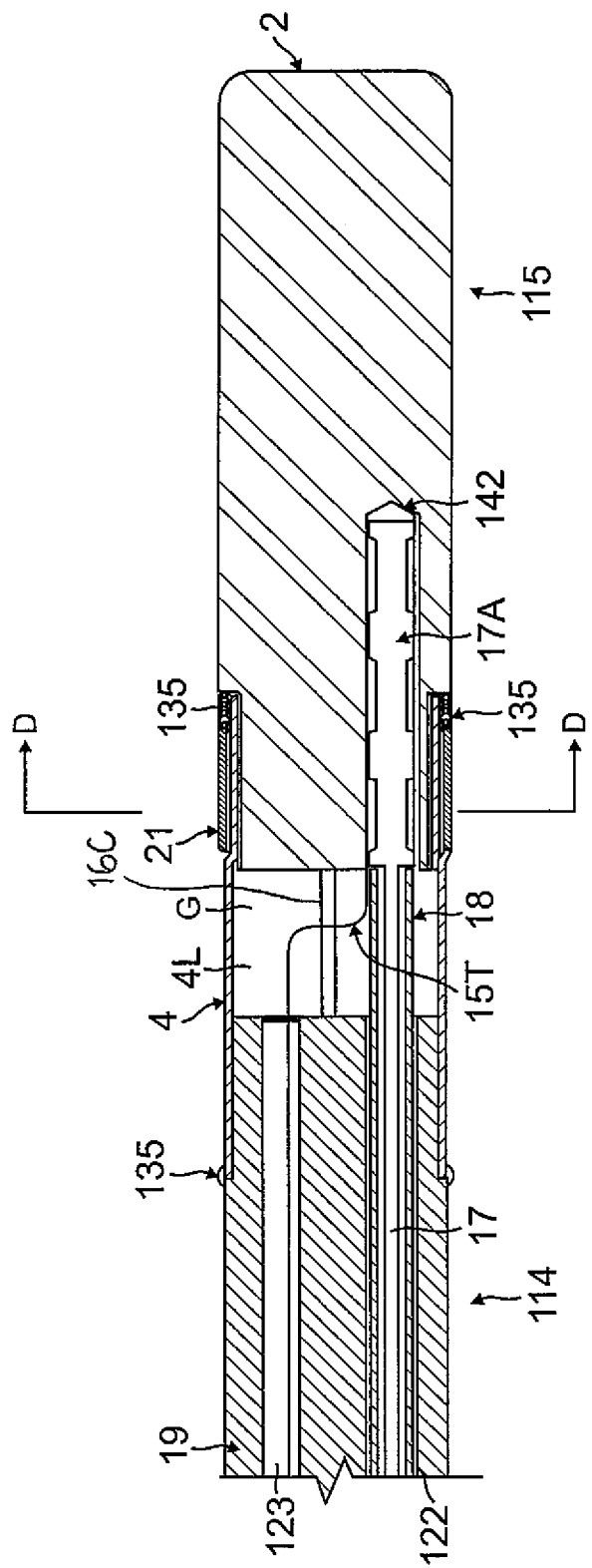

ABLATION CATHETER WITH DEDICATED FLUID PATHS AND NEEDLE CENTERING INSERT

FIELD OF INVENTION

This invention relates to catheters, in particular, cardiac catheters for ablation and tissue diagnostics.

BACKGROUND

Radiofrequency (RF) ablation of cardiac and other tissue is a well-known method for creating thermal injury lesions at the tip of an electrode. Radiofrequency current is delivered between a skin (ground) patch and the electrode. Electrical resistance at the electrode-tissue interface results in direct resistive heating of a small area, the size of which depends upon the size of the electrode, electrode tissue contact, and current (density). Further tissue heating results from conduction of heat within the tissue to a larger zone. Tissue heated beyond a threshold of approximately 50-55 degrees C. is irreversibly injured (ablated).

Resistive heating is caused by energy absorption due to electrical resistance. Energy absorption is related to the square of current density and inversely with tissue conductivity. Current density varies with conductivity and voltage and inversely with the square of radius from the ablating electrode. Therefore, energy absorption varies with conductivity, the square of applied voltage, and inversely with the fourth power of radius from the electrode. Resistive heating, therefore, is most heavily influenced by radius, and penetrates a very small distance from the ablating electrode. The rest of the lesion is created by thermal conduction from the area of resistive heating. This imposes a limit on the size of ablation lesions that can be delivered from a surface electrode.

Methods to increase lesion size would include increasing electrode diameter, increasing the area of electrode contact with tissue, increasing tissue conductivity and direct mechanical penetration of the tissue by the ablating electrode/needle.

The electrode can be introduced to the tissue of interest directly (for superficial/skin structures), surgically, endoscopically, laparoscopically or using percutaneous transvascular (catheter-based) access. Catheter ablation is a well-described and commonly performed method by which many cardiac arrhythmias are treated. Needle electrodes have been described for percutaneous or endoscopic ablation of solid-organ tumors, lung tumors, and abnormal neurologic structures.

Catheter ablation is sometimes limited by insufficient lesion size. Ablation of tissue from an endovascular approach results not only in heating of tissue, but heating of the electrode. When the electrode reaches critical temperatures, denaturation of blood proteins causes coagulum formation. Impedance can then rise and limit current delivery. Within tissue, overheating can cause steam bubble formation (steam "pops") with risk of uncontrolled tissue destruction or undesirable perforation of bodily structures. In cardiac ablation, clinical success is sometimes hampered by inadequate lesion depth and transverse diameter even when using catheters with active cooling of the tip. Theoretical solutions have included increasing the electrode size (increasing contact surface and increasing convective cooling by blood flow), improving electrode-tissue contact, actively cooling the electrode with fluid infusion, changing the material composition of the electrode to improve current delivery to tissue, and pulsing current delivery to allow intermittent cooling.

Needle electrodes improve contact with tissue and allow deep penetration of current delivery to areas of interest. Ablation may still be hampered by the small surface area of the needle electrode such that heating occurs at low power, and small lesions are created. An improved catheter with needle ablation is disclosed in U.S. Pat. No. 8,287,531, the entire disclosure of which is hereby incorporated by reference.

While needle electrodes improve tissue ablation, the structural integrity of a needle electrode may be compromised by steam pops arising from RF "arcing" between the needle electrode and adjacent conductive components of the catheter, including a tip electrode through which the needle electrode extends. When electrical conduction occurs between the needle electrode and the distal end of the tip electrode, the resulting cavitation or mini-shockwaves produced by the steam pops can cause premature wear and tear on the needle electrode that could lead to breakage and detachment from the catheter.

The "arcing" may be reduced by increasing the distance, especially the radial distance, between the needle electrode and the tip electrode. However, by increasing the distance, the formation of coagulum between the needle electrode and the tip electrode may increase despite surrounding blood flow that typically tends to minimize or prevent coagulum formation.

Accordingly, it is desirable for a catheter to have a distal tip configuration that increases distance, especially radial distance, between the needle electrode and the tip electrode, and provides irrigation between the needle electrode and the tip electrode, especially at the distal end of the tip electrode, to minimize the formation of coagulum. It is also desirable that the irrigation be supplied by a dedicated fluid path with sufficient pressure so as to avoid blood seepage into the catheter while minimizing the risk of trapped air bubbles. It is further desired that the irrigation be supplied circumferentially around the outer surface of the needle electrode for uniform cooling.

SUMMARY OF THE INVENTION

The catheter of the present invention is directed to an improved catheter with an elongated catheter body, a distal tip section with a tip electrode, a needle electrode assembly configured for longitudinal movement relative to the catheter, and a needle centering insert that is received in a channel formed in the tip electrode. The needle electrode assembly has a proximal tubing and a distal needle electrode, and the insert is advantageously configured to support the needle electrode in the channel of the tip electrode at a predetermined separation distance from the tip electrode while enabling irrigation to flow circumferentially around the needle electrode through the channel and exit at the distal end of the tip electrode for uniform cooling and minimizing the formation of coagulum on the distal end of the tip electrode.

The catheter also provides a first dedicated pathway that extends through the needle electrode assembly and exits at the distal end of the needle electrode for passing fluid along the catheter and directly into tissue at the needle electrode ablation site. The catheter also provides a second dedicated pathway to supply fluid to the channel in the tip electrode, wherein the second pathway is defined by a guide tube and directed by a plunger member. The guide tube surrounds the needle electrode assembly throughout its length and is sized to provide a gap with an annular cross-section between the inner surface of the guide tube and the outer surface of the proximal tubing. The plunger member is fixedly positioned on the proximal tubing to maintain a fluid-tight seal with the inner surface of the guide tubing for directing the flow distally, as the needle electrode assembly is extended or retracted longitudinally relative to the catheter. To supply fluid to the annular gap, the second pathway includes a traversal from a lumen in the proximal tubing to the annular gap via a hole formed in the sidewall of the proximal tubing. The location of the plunger member on the proximal tubing is immediately proximal of the hole so as to minimize the risk of trapped air bubbles forming in the second pathway. The first and second fluid pathways are advantageously dedicated and independent of each other so as to assure that the fluid passing through each pathway has a constant flow regardless of whether the needle electrode is extended and insert into tissue or retracted into the tip electrode.

In one embodiment, the catheter comprises an elongated catheter body, a distal tip section having a tip electrode with a needle channel, a needle centering insert having a needle passage, the insert positioned in the needle channel of the tip electrode, and a needle electrode assembly having a proximal tubing extending through at least a lumen in the elongated catheter body and a distal needle electrode extending through the needle passage of the insert, and an injection control handle configured to move the needle electrode assembly into the extended position and the retracted position, wherein the needle passage has an inner surface with at least one groove configured for fluid flow between the insert and the needle electrode extending through the needle channel. The catheter further comprises a fluid path that communicates with the at least one groove, wherein the fluid path has a distal exit at the distal end of tip electrode. The catheter may also comprise a second fluid path extending through at least the catheter body and having a distal exit at the distal end of the needle electrode assembly, wherein the first and second fluid paths are isolated from each other.

In a more detailed embodiment, the needle electrode assembly includes a proximal tubing and a distal needle electrode, and the second fluid path passes through the proximal tubing and the distal needle electrode.

In another embodiment, the catheter comprises an elongated catheter body. a distal tip section having a tip electrode with a distal end, a needle electrode assembly extending through at least the elongated catheter body and the tip electrode, the needle electrode assembly being longitudinally movable relative to the catheter body and distal tip section into an extended position and a retracted position, and an injection control handle proximal of the catheter body configured to move the needle electrode assembly into the extended position and the retracted position. The catheter further comprises a first fluid path extending through at least the catheter body and having a distal exit at the distal end of the tip electrode, and a second fluid path extending through at least the catheter body and having a distal exit at the distal end of the needle electrode assembly, wherein the first and second fluid paths are isolated from each other.

In a more detailed embodiment, the needle electrode assembly of the catheter has an elongated proximal tubing extending through the catheter body, and a distal needle electrode extending through the tip electrode. The catheter also has a needle centering insert, wherein the tip electrode has a longitudinal passage that receives the needle centering insert, the needle centering insert having a needle passage through which needle electrode extends. An inner surface of the insert lining the needle passage has a cross-section with a smaller diameter forming a peak and a larger diameter forming a valley, wherein the peak supports the needle electrode in the needle passage and the valley allows fluid to pass along the outer surface of the needle electrode.

In a more detailed embodiment, the catheter includes a guide tube that surrounds the needle electrode assembly along its length, but sized to leave a gap with an annular cross-section between the assembly and the guide tube. The first fluid path passes through the needle electrode assembly. The second fluid path has a proximal portion that extends through the needle electrode assembly, a distal portion that extends through annular gap, and a traversal portion that connects the proximal portion and the distal portion via hole in the side wall of the needle electrode assembly.

In a more detailed embodiment, the needle electrode assembly includes a proximal tubing having a plunger member on its outer surface that forms a seal against an inner surface of the guide tube, wherein the plumber member maintains the seal as the needle electrode assembly moves longitudinally relative to the catheter body.

BRIEF DESCRIPTION OF THE DRAWINGS

These and other features and advantages of the present invention will be better understood by reference to the following detailed description when considered in conjunction with the accompanying drawings wherein:

FIG. 3C is the side cross-sectional view of the distal tip section of FIGS. 3A and 3B, taken along the second diameter.

FIG. 4A(1) is a perspective view of a needle centering insert, in accordance with one embodiment of the present invention.

FIG. 4A(2) is another perspective view of the needle centering insert FIG. 4A(1).

DETAILED DESCRIPTION OF THE INVENTION

Figure 1:
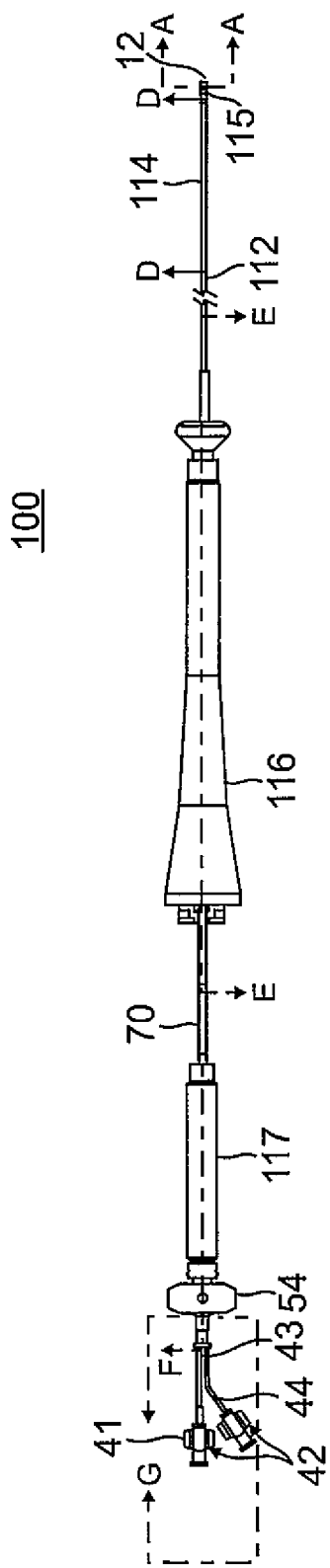
FIG. 1 is a perspective view of a catheter of the present invention, in accordance with one embodiment.

As shown in FIG. 1, the catheter 100 comprises an elongated catheter body 112, an intermediate deflection section 114, a distal tip section 115, a deflection control handle 116 attached to the proximal end of the catheter body 112, and a needle injector control handle 117 attached indirectly to the catheter body 112 proximal of the deflection control handle 116.

Figure 2A:
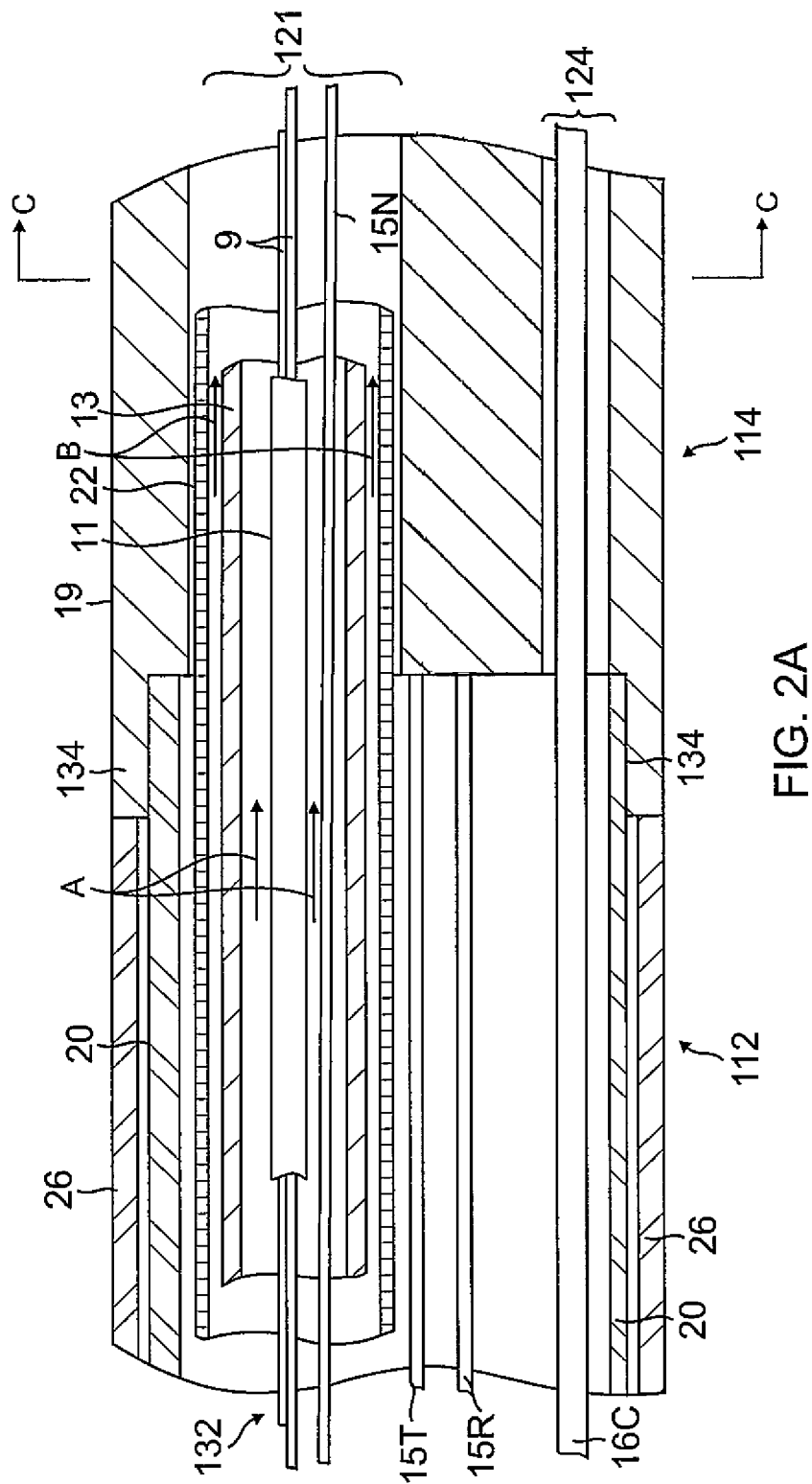
FIG. 2A is a side cross-sectional view of the catheter of FIG. 1, including a junction between a catheter body and the deflection section.
Figure 2B:
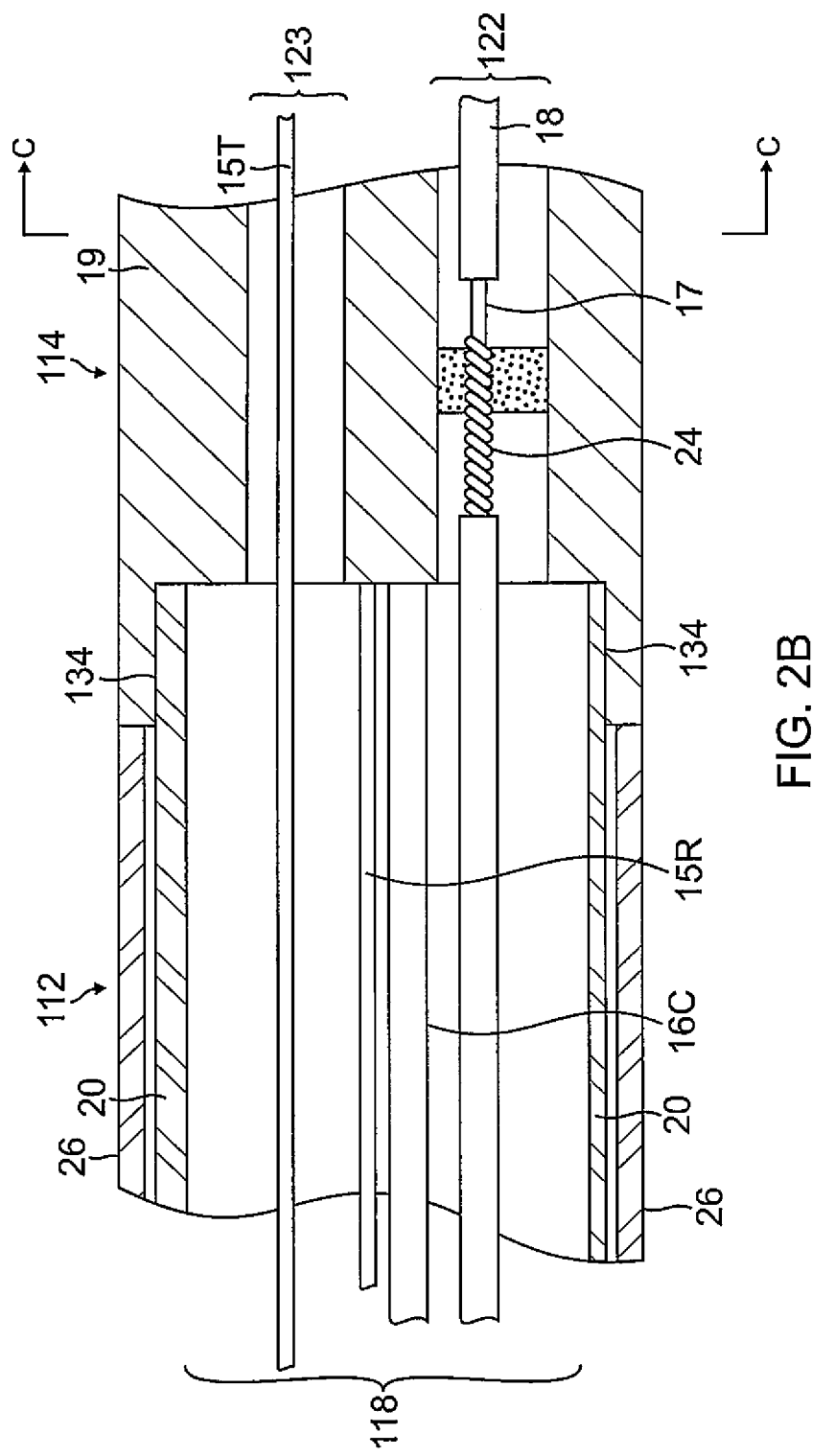
FIG. 2B is a side cross-sectional view of the catheter of FIG. 1, including a junction between the catheter body and the deflection section, along a second diameter generally perpendicular to the first diameter of FIG. 2A.

With reference to FIGS. 2A and 2B, the catheter body 112 comprises a single, central or axial lumen 118. The proximal shaft 112 is flexible, i.e., bendable, but substantially non-compressible along its length. The catheter body 112 may be of any suitable construction and made of any suitable material. In one embodiment, the catheter body 112 comprises an outer wall 26 made of PEBAX®, polyurethane or nylon. The outer wall 26 comprises an imbedded braided mesh of stainless steel or the like to increase torsional stiffness of the catheter body 112 so that, when the deflection control handle 116 is rotated, the catheter body 112 and the distal remainder of the catheter rotate in a corresponding manner.

The outer diameter of the catheter body 112 is not critical, but in one embodiment it is preferably no more than about 8 French. Likewise the thickness of the outer wall 26 is not critical. In the depicted embodiment, the inner surface of the outer wall 26 is lined with a stiffening tube 20, which can be made of any suitable material, preferably polyimide. The stiffening tube 20, along with the braided outer wall 26, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 26.

Figure 2C:
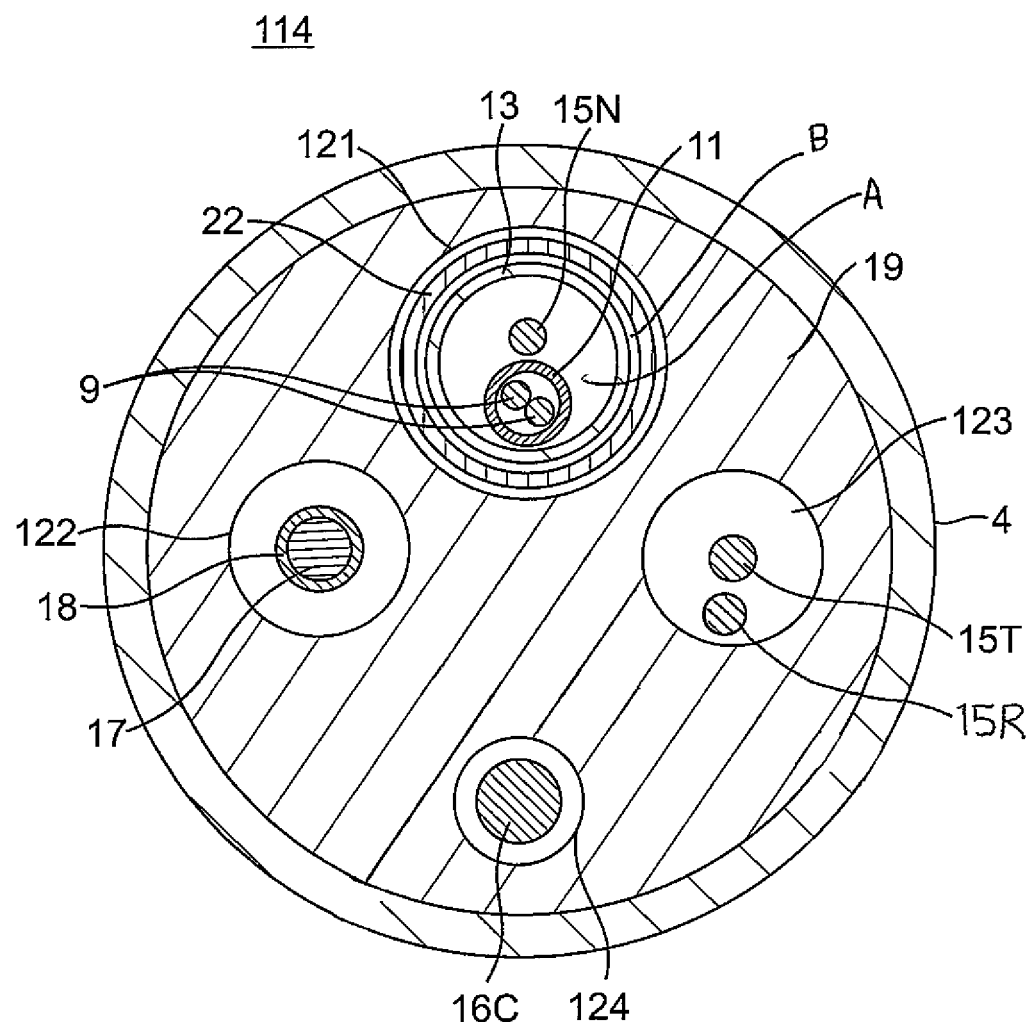
FIG. 2C is an end cross-sectional view of the deflection section of FIGS. 2A and 2B, taken along line C-C.

As shown in FIGS. 2A, 2B and 2C, the intermediate deflection section 114 comprises a shorter section of multi-lumened tubing 19 having, for example, at least four lumens, namely a first lumen 121, a second lumen 122, a third lumen, and a fourth lumen 124, most if not all of which are off-axis. The tubing 19 is made of a suitable non-toxic material that is preferably more flexible than the catheter body 12. A suitable material for the tubing 19 is braided polyurethane, i.e., polyurethane with an embedded mesh of braided stainless steel or the like. The outer diameter of the intermediate deflection section 114, like that of the catheter body 112, is in the disclosed embodiment no greater than about 8 French.

A suitable means for attaching the catheter body 112 to the intermediate deflection section 114 is illustrated in FIGS. 2A and 2B. The proximal end of the intermediate deflection section 114 comprises an inner counter bore 134 that receives the outer surface of the distal end of the stiffener 20. These ends are attached by glue or the like. Other methods for attaching can be used in accordance with the invention.

The stiffening tube 20 is held in place relative to the outer wall 26 at the catheter body 112. In a suitable construction of the catheter body 112, a force is applied to the proximal end of the stiffening tube 20, which causes the distal end of the stiffening tube 20 to firmly push against the counter bore 134. While under compression, a first glue joint is made between the stiffening tube 20 and the outer wall 26 by a fast drying glue, e.g. Super Glue®. Thereafter, a second glue joint is formed between the proximal ends of the stiffening tube 20 and outer wall 26 using a slower drying but stronger glue, e.g., polyurethane.

The depicted catheter includes a mechanism for deflecting the catheter. In the depicted embodiment, the catheter is adapted for uni-directional deflection with a puller wire 17 extending into the second lumen 122. The puller wire is anchored at its proximal end in the deflection control handle 116 and anchored at its distal end in the distal tip section 115. The puller wire is made of any suitable metal, such as stainless steel or Nitinol, and is preferably coated with Teflon® or the like. The coating imparts lubricity to the puller wire. In one embodiment, the puller wire has a diameter ranging from about 0.006 to about 0.010 inches.

To effectuate deflection along the deflection section. 114, the puller wire is surrounded by a compression coil 24 that extends from the proximal end of the catheter body 112 and terminates at or near the proximal end of the deflection section 114. The compression coil 24 is made of any suitable metal, for example, stainless steel. The compression coil 24 is tightly wound on itself to provide flexibility, i.e., bending, but to resist compression. The inner diameter of the compression coil 24 is preferably slightly larger than the diameter of the puller wire. For example, when the puller wire has a diameter of about 0.007 inches, the compression coil preferably has an inner diameter of about 0.008 inches. The Teflon® coating on the puller wire allows it to slide freely within the compression coil 24. Along its length, the outer surface of the compression coil 24 is covered by a respective flexible, non-conductive sheath to prevent contact other components inside the catheter body 112. The non-conductive sheath may be made of polyimide tubing. Each compression coil 24 is anchored at its proximal end to the proximal end of the stiffening tube 20 in the catheter body 112 by glue (not shown). At its distal end, the compression coil 24 is anchored in the second lumen 122 by a glue joint. Within the deflection section 114, the puller wire 17 extends through a protective sheath 18, for example of Teflon®, which prevents the puller wire from cutting into the wall of the tubing 19 when the deflection section is 114 is deflected. Any other suitable technique for anchoring the puller wire 17. Moreover, bi-directional deflection may be provided with the use of a second puller wire as known in the art.

Longitudinal movement of the puller wire relative to the catheter body 112, which results in deflection of the deflection section 114, is accomplished by suitable manipulation of the control handle 16 (FIG. 1). Examples of suitable control handles manipulating a single puller wire for unidirectional deflection are disclosed, for example, in U.S. Pat. Nos. Re 34,502, 5,897,529 and 6,575,931, the entire disclosures of which are incorporated herein by reference. Suitable control handles manipulating at least two puller wires for bidirectional deflection are described in U.S. Pat. Nos. 6,123,699, 6,171,277, and 6,183,463, the disclosures of which are incorporated herein by reference.

Figure 3A:
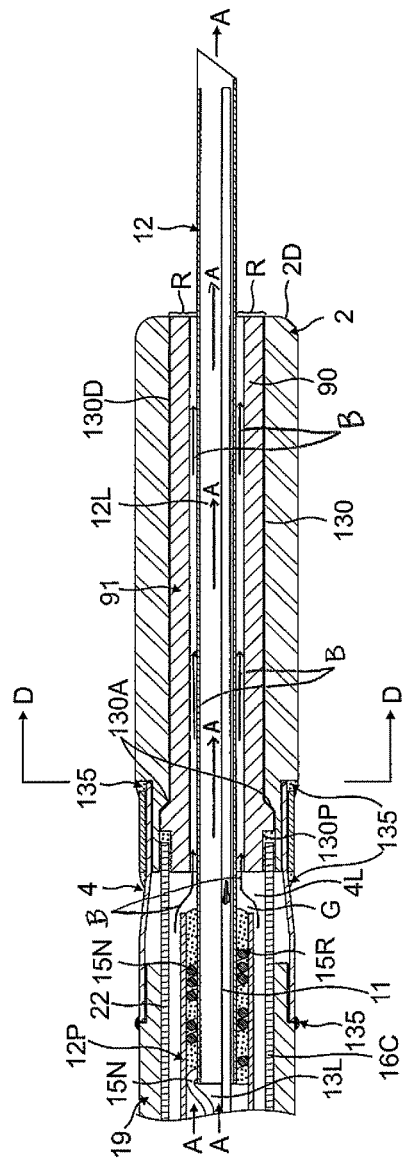
FIG. 3A is a side cross-sectional view of a distal tip section of the catheter of FIG. 1, including a needle electrode assembly of the present invention in an extended position, taken along the first diameter.

Extending through the catheter body 112 and into the distal tip section 115 is an irrigated ablation needle electrode assembly 132, as shown in FIG. 3A. The assembly 132 comprises a proximal tubing 13 and a distal electrode needle 12. The proximal tubing 13 extends through the central lumen 118 of the catheter body 112 and the lumen 121 of the tubing 19 of the deflection section 114 (FIGS. 2A and 2C). The distal electrode needle 12 extends through the distal tip section 115, although the assembly 132 as a whole is longitudinally movable relative to catheter body 112 and the distal tip section 115, between a retracted, withdrawn position (FIG. 3B) and an extended, deployed position (FIG. 3A).

Figure 3B:
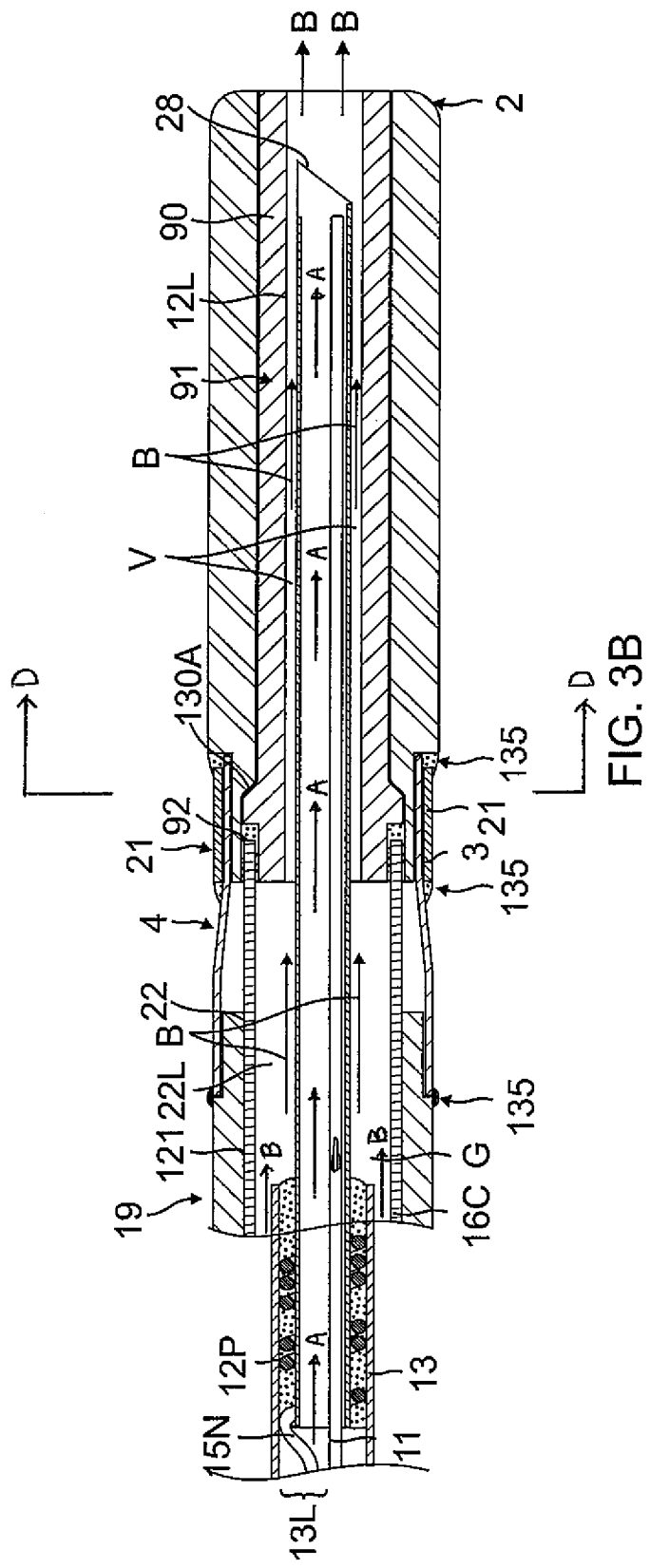
FIG. 3B is a side cross-sectional view of the distal tip section of FIG. 3A, including the needle electrode assembly in a retracted position.

As shown in FIGS. 3A, 3B and 3C, the distal tip section 115 includes a tip electrode 2 and a connector tubing 4. The tip electrode 2 has a longitudinal channel 130, with a circular cross-section, through which the distal electrode needle 12 extends. The channel 130 has a shorter proximal portion 130P with a larger diameter, a longer distal portion 130D with a smaller diameter, an annular abutment or stop 130A at a junction therebetween.

A proximal end of the tip electrode 2 is attached to the tubing 19 of the deflection section 114 by the connector tubing 4 whose proximal end is mounted over a notched' outer surface of the distal end of the tubing 19 and whose distal end is mounted over a notched proximal end of the tip dome electrode 2. The tubing 4, which may be constructed of any suitable material, for example, PEEK (polyimide or polyether etherketone), has a central lumen 4L and a length that provides an axial separation gap G between the tubing 19 and the tip electrode 2 so that components extending therebetween can bend and reorient/realign as needed. A ring electrode 21 is mounted over connector tubing 4 and the proximal end of the tip electrode 2. An adhesive sealant 135, for example, polyurethane, is applied to the proximal and distal ends of the connector tubing 4 to secure attachment.

Figure 3D:
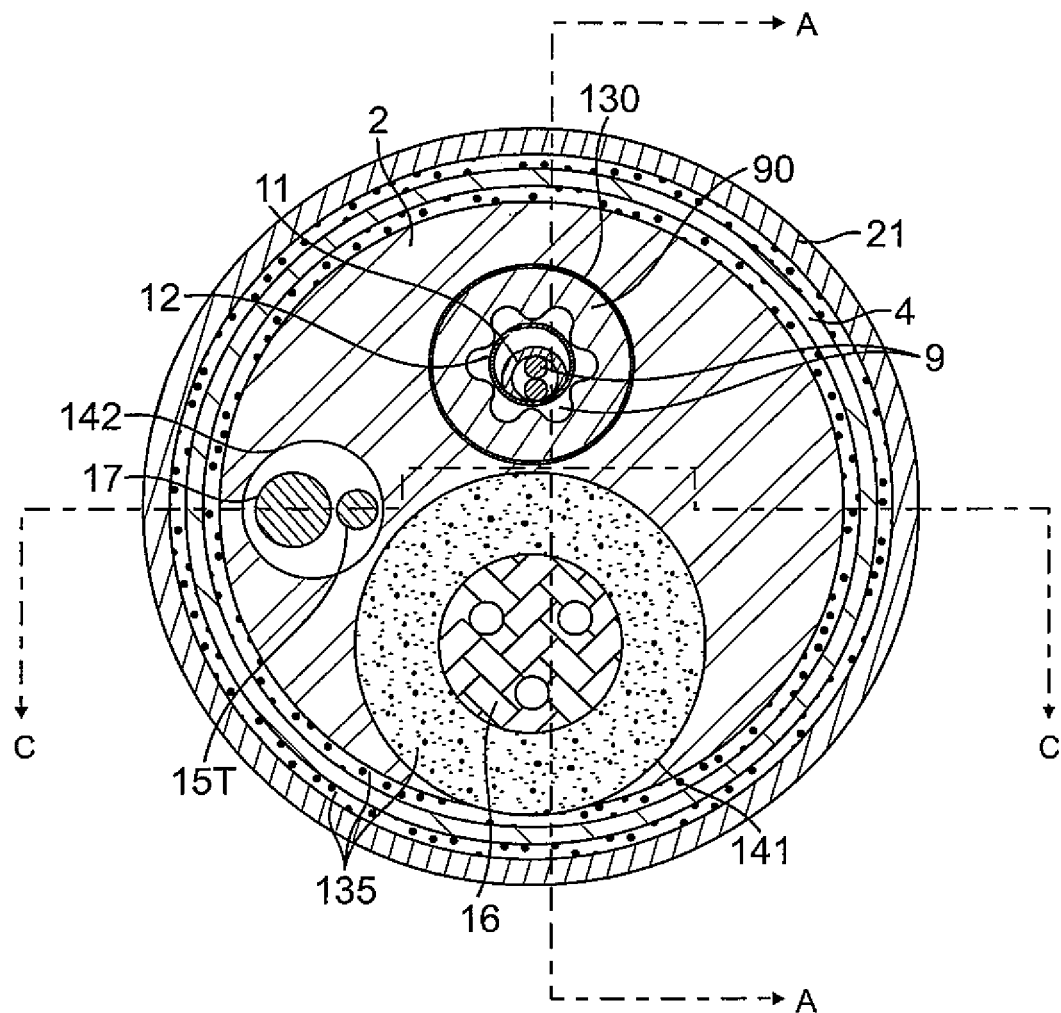
FIG. 3D is an end cross-sectional view of the distal tip section of FIGS. 3A, 3B and 3C, taken along line D-D.

With reference to FIG. 3D, a proximal face of the tip electrode 2 is formed with multiple blind holes 141 and 142. The blind hole 141 is generally aligned with the lumen 124 of the deflection section 114 and receives an electromagnetic position biosensor 16. The blind hole 142 is generally axially aligned with the lumen 122 of the deflection section 114 and receives a distal end of the puller wire 17, including an anchor 17A, for example, a stainless steel hypo stock crimped onto the distal end of the puller wire, that is soldered or otherwise potted in the blind hole 142. The blind hole 142 also receives a distal end of a lead wire 15T extending from the lumen 123 of the deflection section 114 and the central lumen 118 of the catheter body 112. The lead wire 15T, which is provided for the tip electrode 2, readily bends as needed in the axial gap G between the lumen 123 and the blind hole 142.

The tip dome electrode 2 and the ring electrode 21 may be constructed of any suitable material, including platinum, iridium, palladium or a combination thereof. Lead wire 15N is provided for the needle electrode 12 and the lead wire 15R is provided for the ring electrode 21. The lead wire 15R extends from the deflection control handle 116, through the lumen 118 of the catheter body 112, and the lumen 123 of the deflection section 114 and into the axial gap G where its distal end is connected to the ring electrode 21 through an opening 3 (FIG. 3B) formed in the side wall of the connector tubing 4. The path of the lead wire 15N in the catheter is explained further below.

The needle electrode assembly 132 is used to ablate tissue while simultaneously injecting saline or other fluid to conduct the ablation energy and cool the needle electrode. The saline in the perfused tissue increases the effective size of the ablation electrode. The needle electrode assembly 132 is extendable and retractable by manipulation of the needle control handle 17 (FIG. 1), as described further below. FIG. 3A depicts the needle electrode assembly 132 in an extended position relative to the catheter as it would be to ablate and/or monitor electrograms from the tissue. The needle electrode 12 may be returned or withdrawn into the channel 130, as shown in FIG. 3B, to avoid damage to its distal end and/or injury to the patient, particularly while the catheter is advanced through the vasculature of a patient's body and while the catheter is removed from the body.

The needle electrode assembly 132 extends through the injection control handle 117, the deflection control handle 116, the catheter body 112, and the deflection section 114 and into the distal tip section 115, as shown in FIG. 3A. In the disclosed embodiment, the proximal tubing 13 extends from the needle control handle 117, through the deflection control handle 16, through the lumen 118 of the catheter body 112, and into the first lumen 131 of the deflection section 114. The elongated flexible proximal tubing 13 with lumen 13L is connected to the needle electrode 12 which is a generally rigid, electrically-conductive tubing that is hollow with a lumen 12L. The generally rigid nature of the needle electrode 12 (used herein interchangeably with "electrode needle") allows it to pierce tissue in order to increase its effectiveness during ablation. In one embodiment, the needle electrode 12 is formed of Nitinol or stainless steel, and, as illustrated, is formed with a beveled edge 28 at its distal tip to enhance its ability to pierce tissue. The proximal tubing 13 may be made PEEK, but may be made of any other suitable biocompatible material, such as plastic or metal.

In the illustrated embodiment, the proximal tubing 13 and the needle electrode 12 are joined whereby a proximal end of the needle electrode 12 is received in the lumen 13L of the proximal tubing 13 at its distal end. As such, the lumen 13L of the proximal tubing 13 communicates with and is directly connected to the lumen 12L of the needle electrode 12. Fluid in the lumen 13L can therefore pass into the lumen 12L and exit from the catheter at the distal end of the needle electrode 12 as shown by arrows A. As described further below, the fluid shown by arrows A passes along a first isolated, independent and dedicated fluid pathway, defined in part by the lumen 13L of the proximal tubing 13 and the lumen 12L of the needle electrode 12. The first fluid path extends from the injection control handle 117, through the deflection control handle 116, and through lumens in the catheter body 112, the deflection section 114 and the needle electrode 12.

Figure 3E:
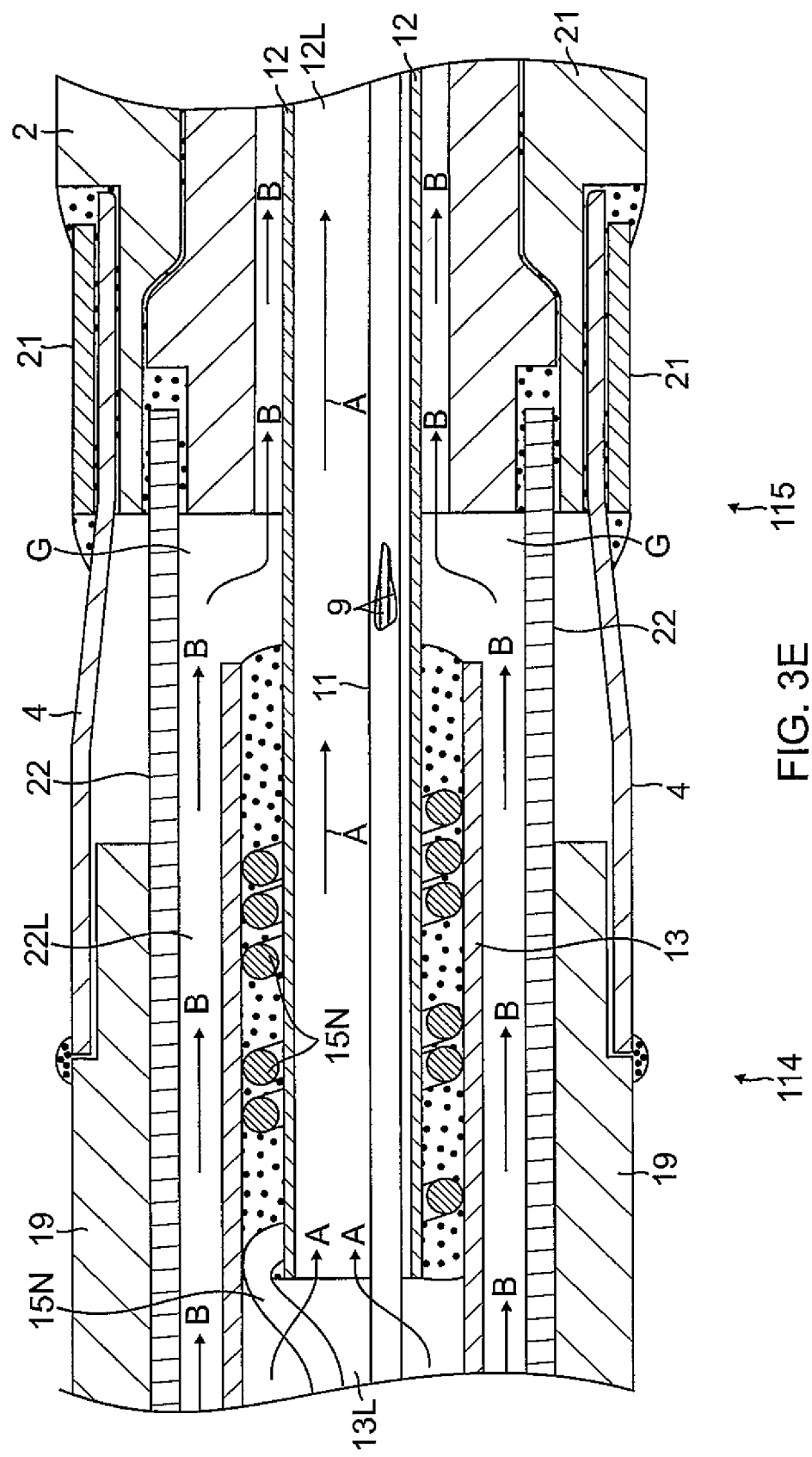
FIG. 3E is a detailed view of a junction between a deflection section and a tip electrode of FIG. 3A.

As shown in FIGS. 3A, 3B and 3E, the lead wire 15N provided for the needle electrode 12 extends through the proximal tubing 13. In the distal end of the proximal tubing 13, a distal portion of the lead wire 15N is coiled and soldered around a proximal portion of the needle electrode 12, wherein the coiled lead wire and the proximal portion of the needle electrode are potted and anchored in the distal end of the proximal tubing 13 by a suitable material, for example, polyurethane 135. The inner diameter of the proximal tubing 13 is sized to accommodate the windings of the lead wire 15N around the proximal portion and surrounding sealant 135. The windings and the sealant together form a fluid-tight sealed joint which securely anchors the electrode needle 12 to the proximal tubing 13. The fluid designated by arrows A is therefore wholly contained within the needle electrode assembly 132 along its entire length, and this pathway is open and available before, during and after any and all longitudinal movement of the needle electrode assembly 132 relative to the catheter in extending and retracting the electrode needle 12.

In accordance with another feature of the present invention, the distal tip section 115 includes a needle centering insert 90 that is fixedly situated in the channel 130 to position and center the needle electrode 12 on-axis within the channel 130, the significance of which is explained further below. As shown in FIGS. 4A(1) and 4A(2), the insert 90 has a generally elongated cylindrical body defining an outer diameter OD. On the outer surface of the insert 90, a raised formation or ring 92 is provided at a predetermined location along the longitudinal axis of the insert closer to the proximal end of the body. The ring 92 is adapted and configured to abut with the stop 130A (FIG. 3A) of the channel 130 of the tip electrode 2 as a safety measure to prevent the insert 90 from slipping out and dislodging from the tip electrode.

The cylindrical body of the insert 90 has a centered, on-axis needle passage 91 which defines an inner diameter ID. The needle electrode 12 extends in and through the needle passage 91. Glued within the channel 130, the outer diameter OD of the insert 90 (as accommodated by the diameter of the channel 130) advantageously provides the desirable radial distance or separation R (FIG. 3A) between the needle electrode 12 and the tip electrode 2, especially at the latter's distal face 2D so as to reduce or minimize electrical "arcing" between the proximal edge of the exposed portion of the needle electrode 12 (extending distally outside of the tip dome electrode) and the distal face 2D when the needle electrode 12 is energized. As such, the insert 90 is made of a nonconductive material, such as PEEK.

Figure 4B:
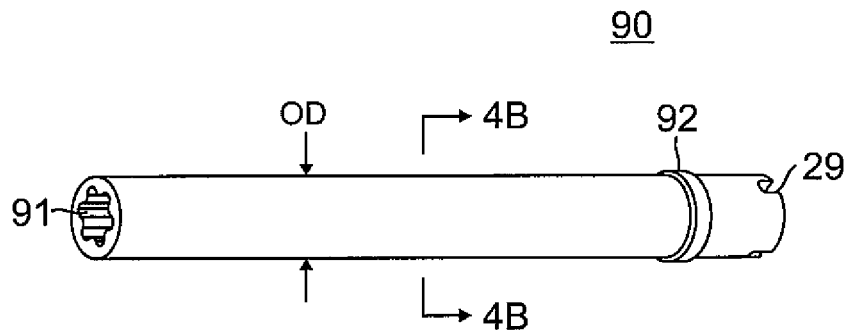
FIG. 4B is an end cross-sectional view of the needle centering insert of FIG. 4A(1) taken along line 4B-4B.
Figure 4B:
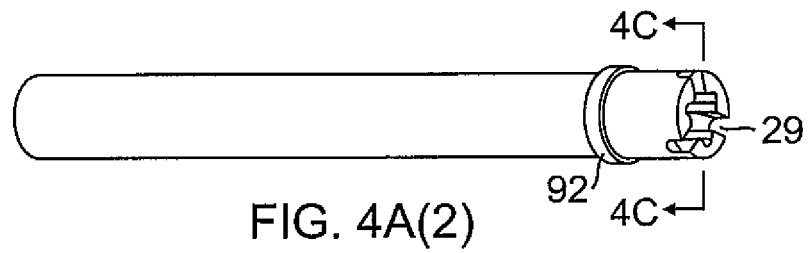
Figure 4B:
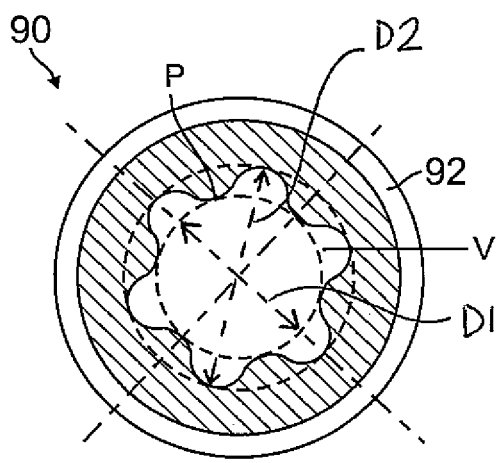
Figure 4C:
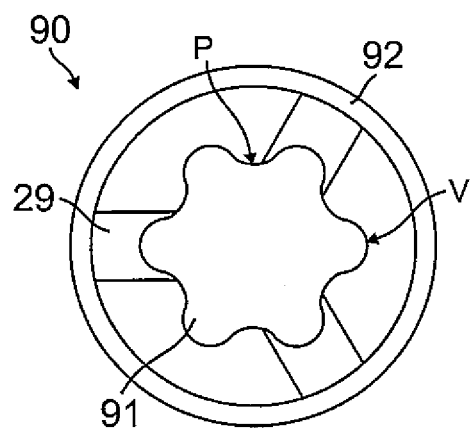
FIG. 4C is an end cross-sectional view of the needle centering insert of FIG. 4A(2) taken along line 4C-4C.
Figure 10:
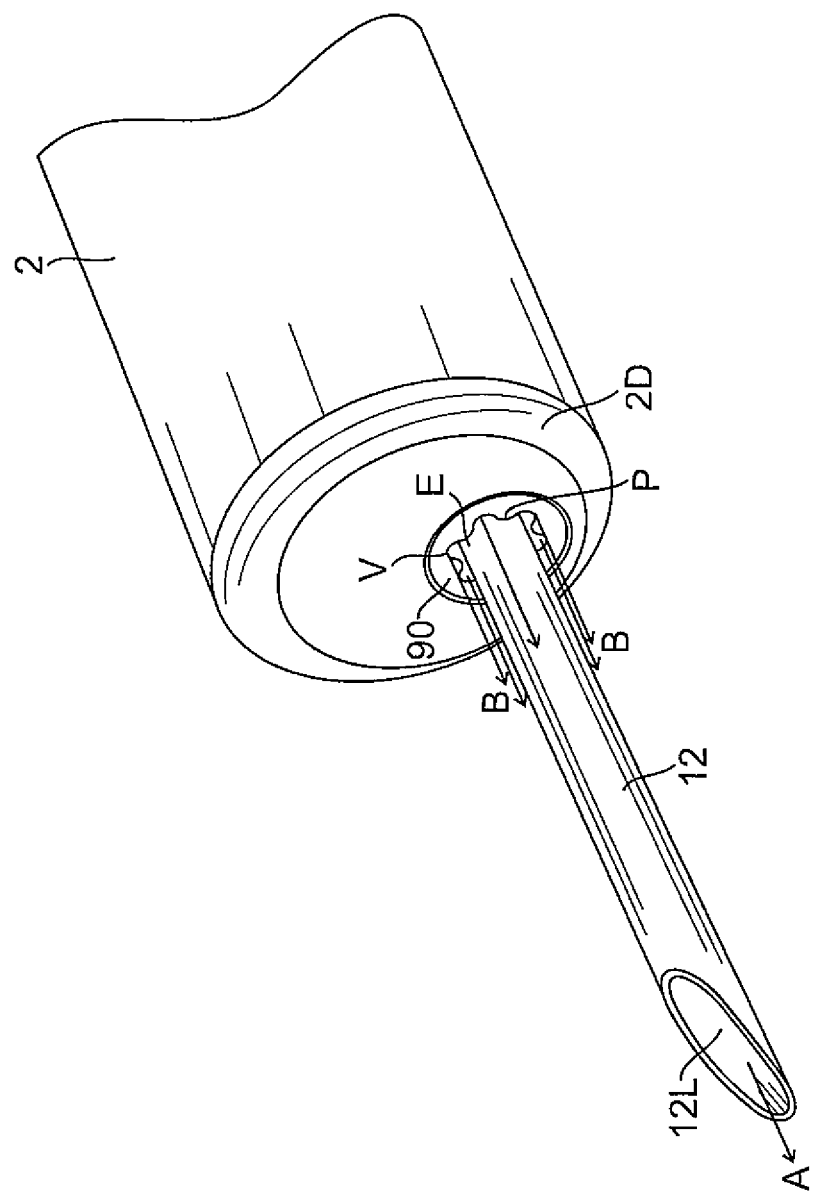
FIG. 10 is a perspective view of a distal end of the catheter, including an extended needle electrode, in accordance with one embodiment of the present invention.

In accordance with a feature of the present invention, the inner surface of the insert 90 lining the needle passage 91 has a cross-section with at least a portion with a smaller diameter that supports the needle electrode 12 centered and on-axis with the needle passage 91 and at least a portion with a larger diameter that provides at least one longitudinal fluid pathway through the needle passage 91 between the inner surface of the insert and the outer surface of the needle electrode 12. In the disclosed embodiment, the inner surface of the insert 90 has an uneven or undulating pattern formed with the larger diameter D1 and the smaller diameter D2 alternating each other about the longitudinal axis of the insert (FIG. 4B), forming longitudinally-spanning peaks P (axial ridges) and valleys V (axial grooves) that run the length of the insert 90 between its distal and proximal ends, as shown in FIGS. 4A(1) and 4A(2). The peaks P are sized uniformly in the radial direction so they provide uniform and simultaneous circumferential support to the needle electrode 12 in order to keep the needle electrode centered and on-axis in the channel 130. The valleys V allow fluid, e.g., saline, to pass distally into the channel 130 along the outer surface of the needle electrode 12, as shown by arrows B (FIGS. 3B and 6A), forming a generally circumferential "sleeve of saline" surrounding the outer surface of the needle electrode 12, and out of the tip dome electrode 2 at the distal face 2D where the sleeve of saline advantageously minimizes the formation of coagulum at the proximal edge E of the exposed needle electrode 12 (FIG. 10). In the disclosed embodiment, the insert 90 is formed with a plurality of six peaks and six valleys evenly distributed in the radial direction. It is understood that the plurality of peaks and valleys may vary as needed or appropriate, for example, each ranging between about three and nine. Moreover, the proximal face of the insert 90 is formed with at least one indented formation or groove 29 (FIGS. 4A(2) and 4C) extending radially and providing communication between at least one valley V and the outer surface of the insert 90 so that fluid can continue to flow from the lumen 13L into the needle passage 91 when the needle assembly 132 is fully extended distally and the distal end of the proximal tubing 13 abuts against the proximal face of the insert 90.

To supply fluid to at least one valley V along the passage 91 between the inner surface of the insert 90 and the outer surface of the needle electrode 12, the catheter 100 includes a first elongated fluid-tight guide tubing 22 (FIGS. 2C, 3A and 3B), with lumen 22L, that surrounds the proximal tubing 13 generally along its entire length between the injection control handle 117 and the needle electrode 12 but is sized to leave a gap with an annular cross-section between its inner surface and the outer surface of the proximal tubing. The sidewall of the guide tubing 22 provides a fluid tight seal along the length of the proximal tubing 13 in the injection control handle 117, the deflection control handle 116, the catheter body 112 and the deflection section 114. A distal end of the fluid-tight tubing 22 is mounted over the proximal end of the insert 90 and abuts with the proximal face of the ring 92 of the insert 90. Accordingly, with the insert 90 being affixed in the tip electrode 2, the guide tubing 22 is not afforded longitudinal movement relative to the catheter and does not slide with the needle electrode assembly 132. That is, the guide tubing 22 remains stationary relative to the catheter as the needle electrode assembly 132 is extended and retracted through the lumen 22L of the guide tubing 22. An adhesive sealant 135, for example, Polyurethane, is applied to seal the distal end of the guide tubing 22 to the ring 92 of the insert 90 which locks the guide tubing 22 at its distal end to the insert 90 and the tip electrode 2.

The guide tubing 22 surrounding the proximal tubing 13 extends through the lumen 121 (FIGS. 2A and 2C) of the tubing 19 of the deflection section 114 and the lumen 118 of the catheter body 112. The guide tubing 22 further extends through the deflection control handle 116 and terminates at its proximal end in the injection control handle 117. In the injection control handle 117, the guide tubing 22 is surrounded by a shorter protective tubing 25, made of, for example, polyamide nylon or ZYTEL, that surrounds the guide tubing 22 in the needle control handle 117. The protective tubing 25 is glued to the guide tubing 22 and thus is also stationary relative to the control handle 117. Accordingly, the fluid shown by arrows B passes along a second isolated, independent and dedicated second fluid pathway, defined by the annular gap in the lumen 22L between the guide tubing 22 and the proximal tubing 13, the grooves 29 on the proximal face of the insert 90, and the valleys V of the insert 90 (FIG. 3B). The second fluid path extends from the injection control handle 117, through the deflection control handle 116, the catheter body 112, the deflection section 114 and the distal tip electrode 2. The fluid designated by arrows B is therefore contained within the guide tubing 22 and the insert 90, and this pathway is generally unaffected and undisturbed by either longitudinal movement of the needle electrode assembly 132 or by the first pathway designated by arrows A defined in the needle electrode assembly 132, as described above. In accordance with a feature of the present invention, each of the first and second pathways is generally separate and independent of each other.

Figure 5:
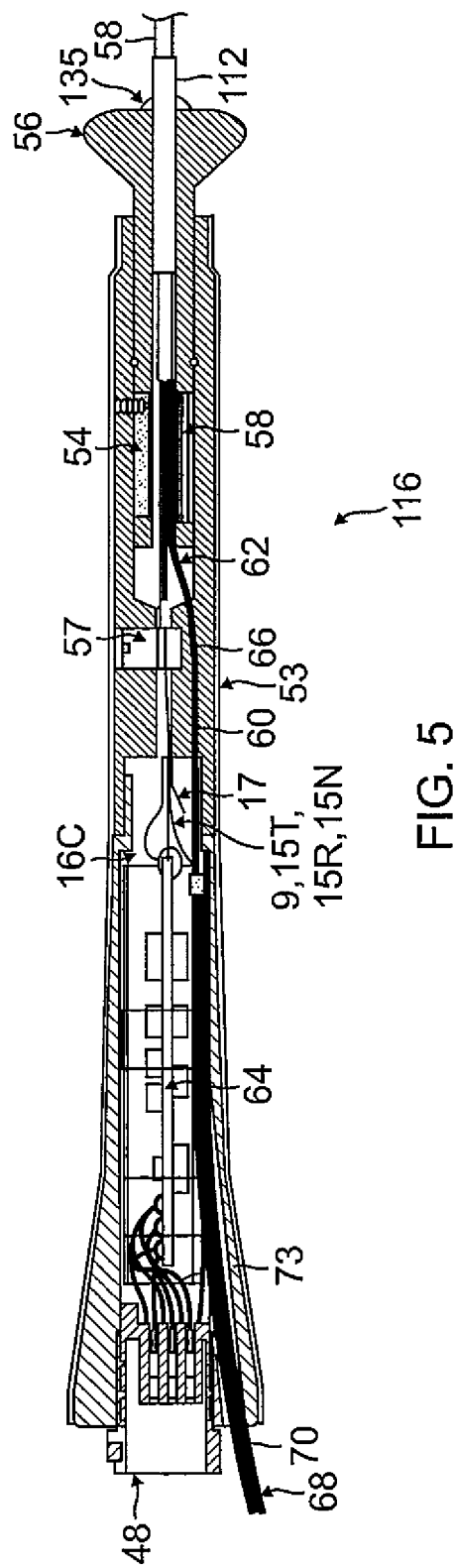
FIG. 5 is a side cross-sectional view of a deflection control handle, in accordance with one embodiment of the present invention.

Longitudinal movement of the puller wire 17 relative to the catheter, which results in deflection of the deflection section 114 is accomplished by suitable manipulation of the control handle 16. As shown in FIG. 5, the distal end of the control handle 16 comprises a barrel 53, a piston 54 with a thumb control 56 longitudinally slidable in the barrel 53 for manipulating the puller wire 17. The proximal end of the catheter body 112 is connected to the piston 54 by means of a shrink sleeve 58.

Components including the puller wire 17, the lead wires 15T, 15N and 15R, the electromagnetic sensor cable 16C, and the proximal tubing 13 along with the components passing therethrough extend through the piston 54. The puller wire 17 is anchored to an anchor pin 57 located proximal of the piston 54. The lead wires 40 and electromagnetic sensor cable 74 extend through a first tunnel 58, located near the side of the control handle 16. The electromagnetic sensor cable 16C connects to the circuit board 64 near the proximal end of the control handle 116. Wires 73 connect the circuit board 64 to a computer and imaging monitor (not shown) via an electrical connector 48.

The proximal tubing 13 of the needle assembly 132 extends through a guide tube 66 at the proximal end of the deflection control handle 116 and is afforded longitudinal movement therein. The guide tube 66 is made of any suitable material, for example, polyurethane, and is anchored to the piston 54 in the first tunnel 58, for example, by a glue joint. This design allows the needle assembly 132 longitudinal movement within the control handle 116 so that the needle assembly 132 does not break when the piston 54 is adjusted to manipulate the puller wire 17. Within the piston 54, the electromagnetic sensor cable 16C and lead wires 15 pass through a transfer tube and the puller wire 17 passes through another transfer tube to allow longitudinal movement of these components through the glue joint in the first tunnel 58.

The proximal tubing 13 of the needle assembly 132 and guide tube 66 extend through a second tunnel 60 situated near the side of the control handle 116. To avoid undesirable bending of the needle assembly 132, a space 62 is provided between the proximal end of the piston 54 and the distal end of the second tunnel 60. In one embodiment, the space 62 has a length of at least 0.50 inch and more preferably about from about 0.60 inch to about 0.90 inch.

In the proximal end of the control handle 116, the proximal tubing 13, and guide tube 66 extend through a second larger plastic guide tube 68, made of, for example, Teflon®, which affords the guide tube 66 and the proximal tubing 13 longitudinal slidable movement. The second guide tube 68 is anchored to the inside of the control handle 116 by glue or the like and extends proximally beyond the control handle 116. The second guide tube 68 protects the proximal tubing 13 both from contact with the circuit board 64 and from any sharp bends as the guide tube 66 and the proximal tubing 13 emerge from the control handle 116. A suitable deflection control handle is described in U.S. Pat. No. 6,623,474, the entire disclosure of which is hereby incorporated by reference.

Figure 6:
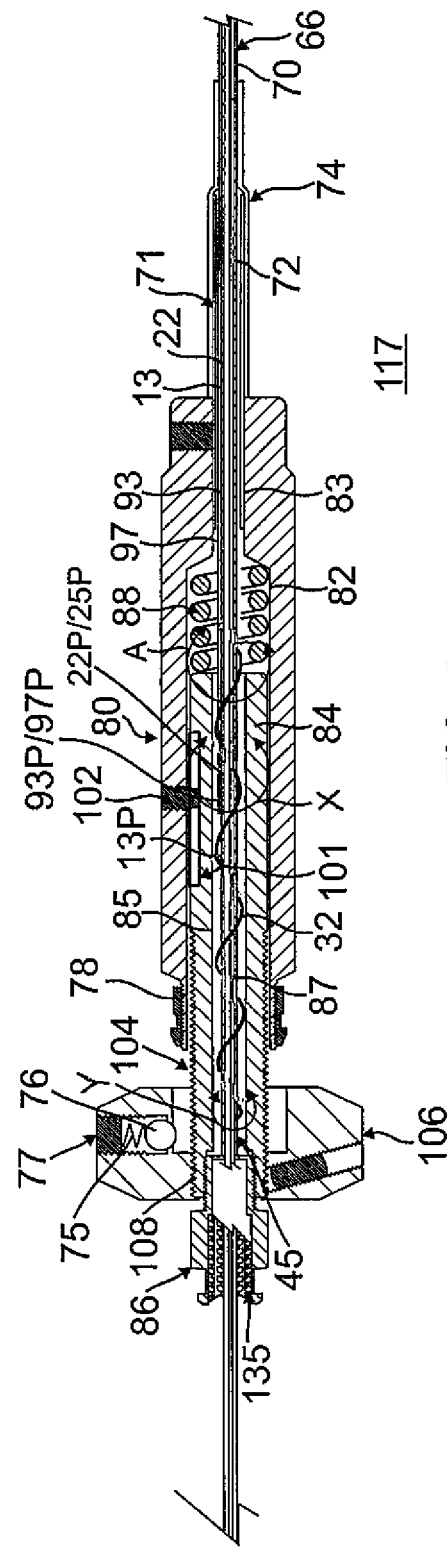
FIG. 6 is a side cross-sectional view of a needle injector control handle, in accordance with one embodiment of the present invention, taken along a first diameter.

Extension and retraction of the needle assembly 132 out the distal end of the tip electrode 2 is accomplished by the needle injection control handle 117. As illustrated in FIG. 6, the needle control handle 117 comprises a generally cylindrical outer body 80 having proximal and distal ends, a piston chamber 82 extending a part of the way therethrough, and a passage 83 extending a part of the way therethrough. The piston chamber 82 extends from the proximal end of the handle part way into the body 80, but does not extend out the distal end of the body. The passage 83, which has a diameter less than that of the piston chamber 82, extends from the distal end of the piston chamber to the distal end of the outer body 80.

A piston 84, having proximal and distal ends, is slidably mounted within the piston chamber 82. A luer connector 86 is mounted in the proximal end of the piston 84. The luer connector 86 is made of a rigid material, for example, stainless steel. The piston 84 has an axial passage 85 through which the proximal tubing 13 of the needle assembly 132 extends, as described in more detail below. A compression spring 88 is mounted within the piston chamber 82 between the distal end of the piston 84 and the outer body 80.

Figure 7:
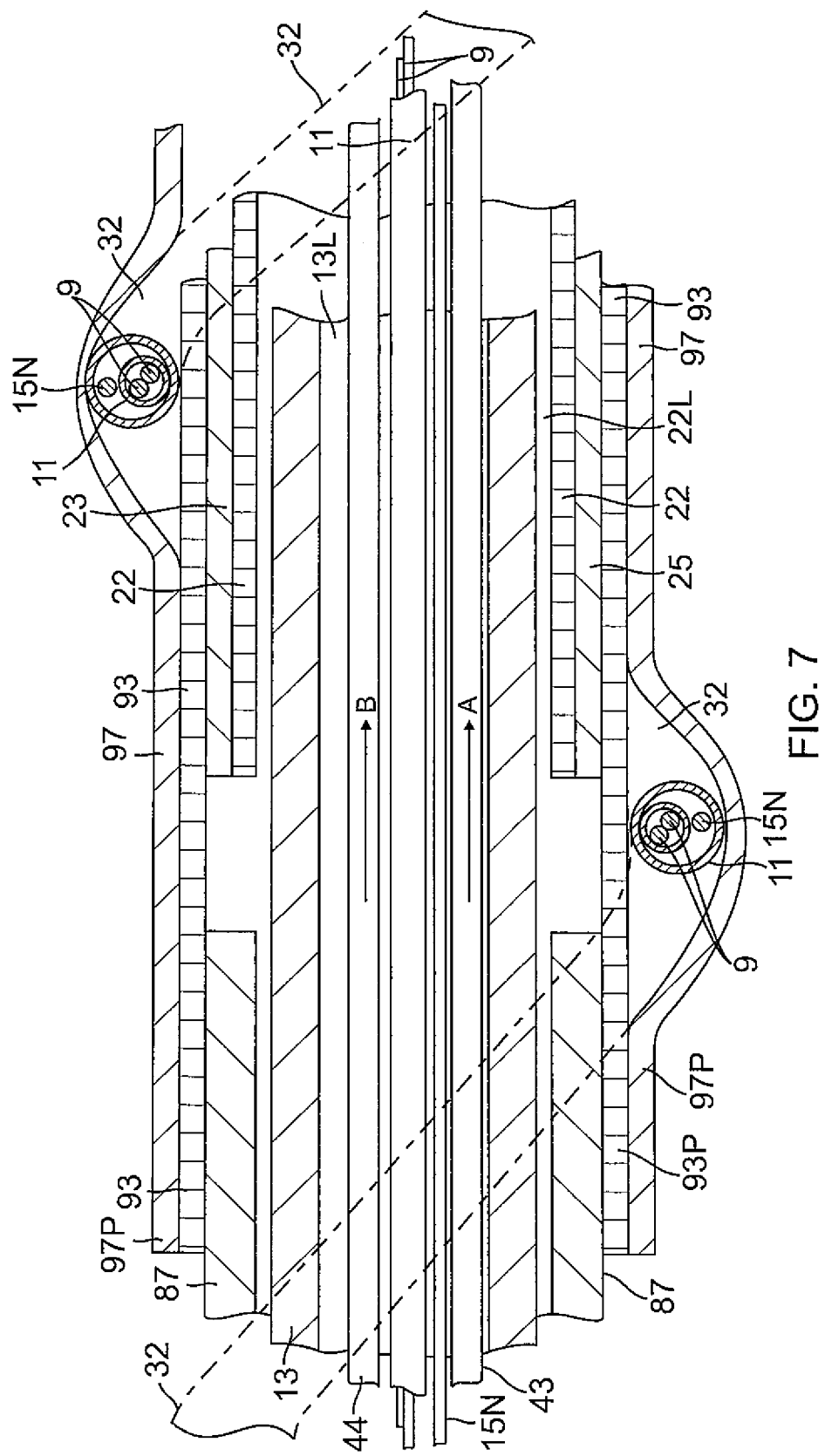
FIG. 7 is a detailed view of the needle injector control handle, including guiding and supporting structures for the needle electrode assembly, of section X of FIG. 6.

As shown in FIGS. 6 and 7, the proximal end of the proximal tubing 13 of the needle assembly 132 is received in lumen 87L of a rigid tubular portion 87 of the luer connector 86. The proximal end of the proximal tubing 13 of the needle assembly 132 is glued or otherwise affixed to the overlapping inner surface of the rigid tubular portion 87 of the luer connector 86. The luer connector 86 is screwed into the piston 84 so that it moves longitudinally with the piston. This arrangement couples longitudinal movement of the luer connector 86 and the piston 84 to the proximal tubing 13 and hence to the needle assembly 132, so that longitudinal movement of the piston 84 extends and retracts the needle assembly 132. The proximal tubing 13 and rigid tubular portion 87 extend through the axial passage 85 of the piston 84. Within the axial passage 85, a rigid tube 93, preferably made of stainless steel, has a proximal end which is coaxial to the distal end of the rigid tubular portion 87. The rigid tube 93 is secured to the needle control handle 117. The shorter tubing 25, glued to the guide tubing 22, is also glued to the rigid tube 93. The rigid tubular portion 87 of the luer connector 86 (along with the proximal tubing 13 of the needle electrode assembly 132 affixed to the rigid tubular portion 87) telescopes in and out of the rigid tube 93. A protective cover or shrink sleeve 97 is applied over the rigid tube 93 to secure the loosely coiled tubing 32 to the rigid tube 93

In use, force is applied to the piston 84 to cause distal movement of the piston relative to the outer body 80, which compresses the compression spring 88. This movement causes the proximal tubing 13 of the needle assembly 132 to correspondingly move distally relative to the outer body 80, tubings 22, 25, 93 and 97 and catheter body 112, so that the distal end of the needle electrode 12 outside the distal end of the tip electrode 2 (FIG. 3A). When the force is removed from the piston, the compression spring 88 pushes the piston 84 proximally to its original position, thus causing the distal end of the needle electrode 12 to retract back into the tip electrode 2 (FIG. 3B). Upon distal movement of the piston 84, the rigid tubular portion 87 moves distally into the rigid tube 91 to align the needle assembly 132 with the composite tubing 22.

The piston 84 further comprises a longitudinal slot 101 extending along a portion of its outer edge. A set screw 102 extends through the outer body 80 and into the longitudinal slot 100. This design limits the distance that the piston can be slid proximally out of the piston chamber 82. When the distal end of the needle electrode 12 is in the retracted position, the set screw 102 is typically at or near the distal end of the longitudinal slot 100.

The proximal end of the piston 84 has a threaded outer surface 104. A circular thumb control 106 is mounted on the proximal end of the piston. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the needle electrode 12 can be extended out the distal end of the catheter. The threaded surfaces of the thumb control 106 and piston 84 allow the thumb control to be moved closer or farther from the proximal end of the outer body 80 so that the extension distance of the needle electrode 12 can be controlled by the user, for example, a physician. The thumb control 106 also incorporates a detent feature, wherein a stainless steel ball 75 is held in place by a spring 76 and set screw 77 so that when the thumb control 106 is advanced over a metal end cap 78 at the proximal end of the outer body 80, the ball 75 holds the thumb control 106 in an advanced position until additional force is used to force the ball 75 over vertical step 78V (FIG. 6) of the metal end cap 78 and release the thumb control 106 from the metal end cap 78. Using the detent feature, the physician can lock the needle electrode assembly 132 in an extended position for the duration of an ablation. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston.

Extending at least between the deflection control handle 116 and the needle control handle 117 are components, including the proximal tubing 13, the lead wire 15N, and thermocouple wires 9 in their protective, nonconducting tubing 11. These components covered by the guide tube 66 pass through a shaft 70 for example, a braided shaft, whose proximal end is received in a rigid tubing 71, for example, a stainless steel tubing, affixed in a distal passage 72 in the distal end of the needle control handle 117 that communicates with the piston chamber 82. A shrink sleeve 74 is mounted partially on the rigid tubing 71 and the shaft 70 to provide strain relief.

The thermocouple wires 9 are provided for sensing temperature of the tip electrode 2. The wires 9 along with the tubing 11, which may be made of polyimide, extend through the needle electrode assembly 132. In the disclosed embodiment, the wires 9 and the tubing 11 extend through the lumen 13L of the proximal tubing 13 and the lumen 12L of the needle electrode 12. Distal ends of the wires 9 and the tubing 11 are coterminous with the distal end of the needle electrode 12. The portion of the tubing 11 extending through lumen 12L may be affixed to the inner surface of the lumen 12L by adhesive sealant 135.

Figure 9:
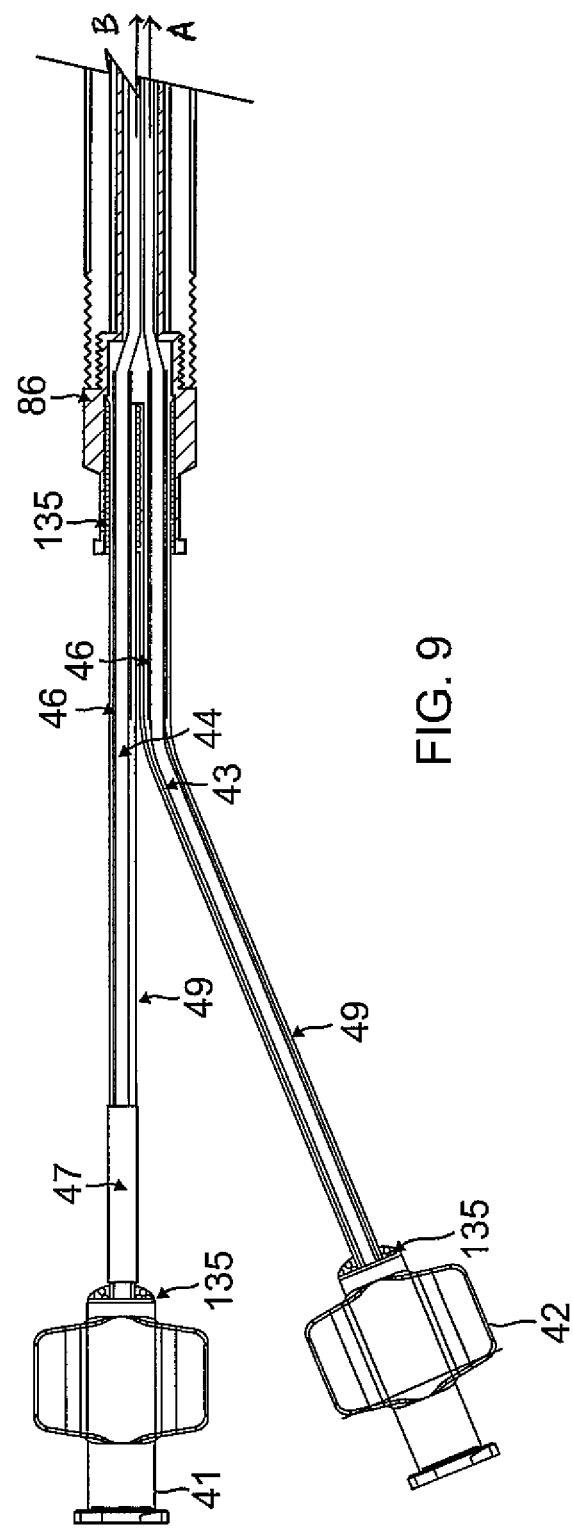
FIG. 9 is a side, partial cross-sectional view of luer hubs connected to the needle injector control handle, in accordance with one embodiment.

As shown in FIG. 9, the catheter includes luer hub 41 and 42 extending off the proximal end of the needle control handle 117. Connected to each luer hub is a respective elongated flexible luer tubings 43 and 44 that enter the proximal end of the needle control handle 117 via the bier connector 86. The luer tubings 43 and 44 may be made of any suitable material, for example, polyimide. Surrounding the portion of each luer tubing 43 and 44 extending between the luers 41 and 42 and the connector luer 86 is a respective protective thick-walled outer shaft 49 whose proximal and distal ends are sealed to the luers 41 and 42, and to the luer connector 86, respectively, by adhesive sealant, e.g., polyurethane 135. A respective shorter tubing 46 constructed of any suitable material, for example, polyimide, may line the interior of the outer shafts 49 to surround the distal portion of each luer tubing 43 and 44 at or near the proximal end of the luer connector 86. A visual marker, e.g., a shrink sleeve 47, may be mounted on a selected tubing 43 or 44 to distinguish one tubing from the other.

Figure 6A:
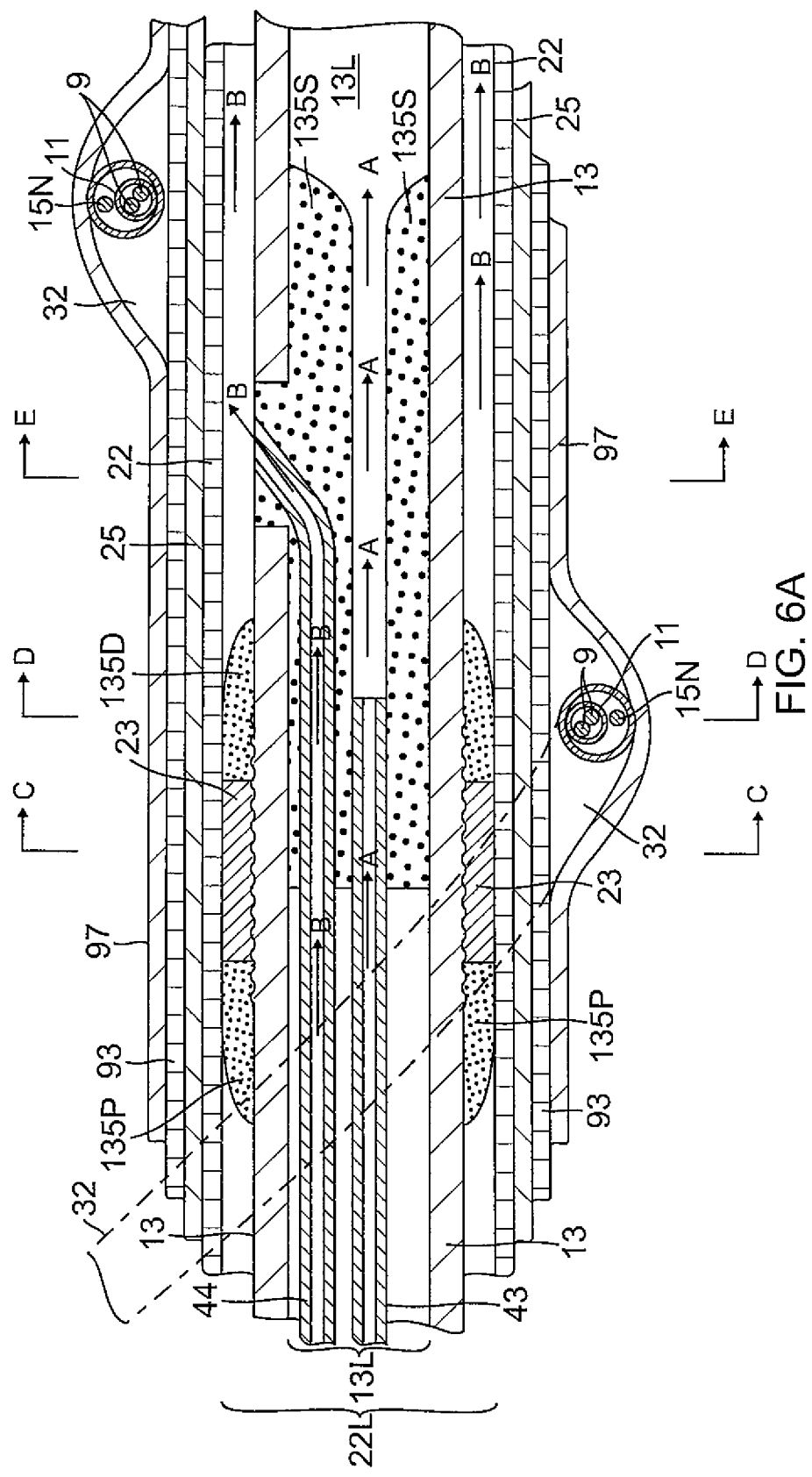
FIG. 6A is a detailed view of the needle injector control handle, including the needle electrode assembly, of section A of FIG. 6.
Figure 6B:
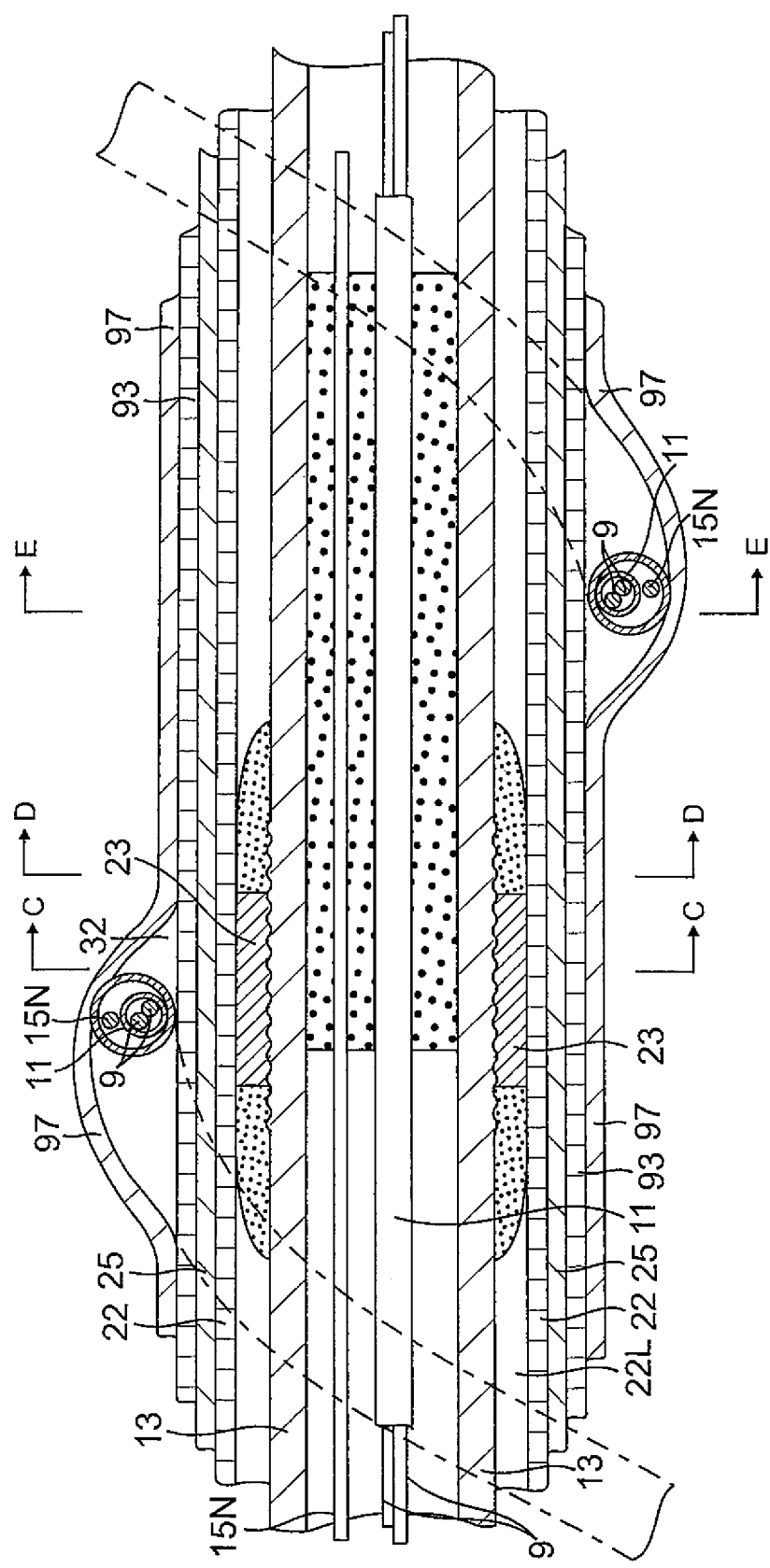
FIG. 6B is a side cross-sectional view of a needle injector control handle of FIG. 6, taken along a second diameter.
Figure 6C:
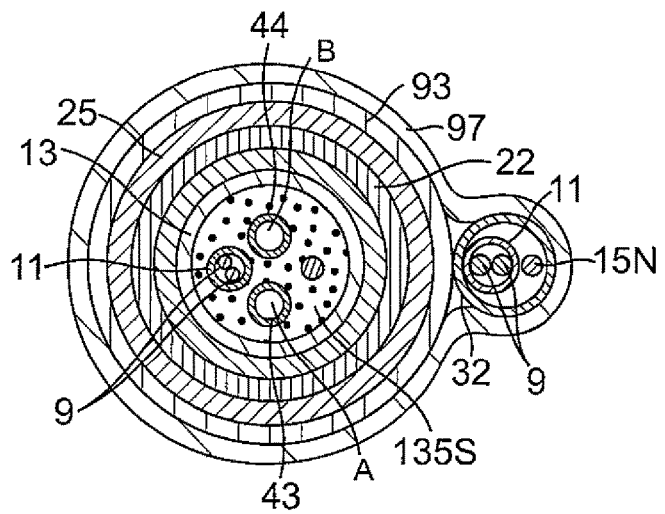
FIG. 6C is an end cross-sectional view of the needle injector control handle, including the needle electrode assembly taken along line C-C.
Figure 6D:
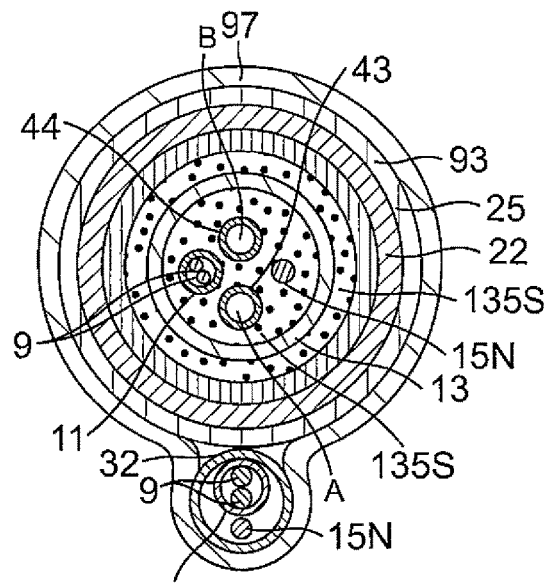
FIG. 6D is an end cross-sectional view of the needle injector control handle, including the needle electrode assembly taken along line D-D.
Figure 6E:
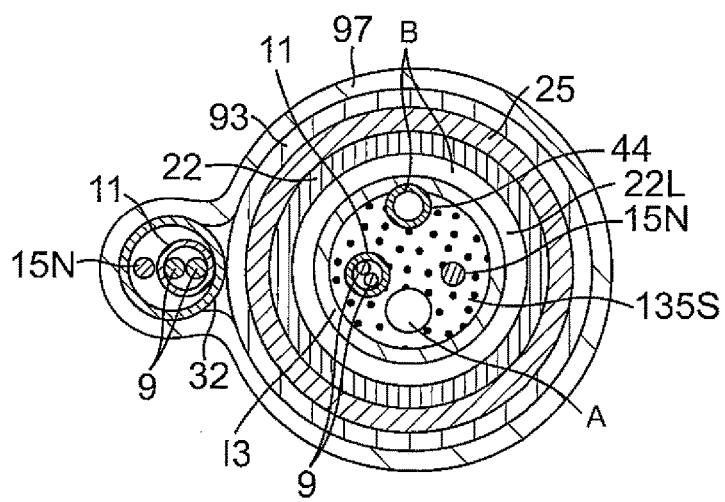
FIG. 6E is an end cross-sectional view of the needle injector control handle, including the needle electrode assembly taken along line E-E.

In the injection control handle 117, within the axial passage 85 of the piston 84, as shown in FIGS. 6 and 6A, both luer tubings 43 and 44 extend through the distal tubular portion 87 of the luer connector 86 and into the proximal end 13P of the proximal tubing 13 of the needle electrode assembly 132. In the illustrated embodiment of FIG. 6, the proximal end of the proximal tubing 13 is proximal of the proximal ends 93P and 97P of the rigid tubing 93 and the protective tubing 97 which, in turn, are proximal of the proximal ends of the tubings 22 and 25.

The luer tubings 43 and 44 extend from their proximal ends in the luer hubs 41 and 42, respectively, to their distal ends at a predetermined location along the longitudinal axis of catheter. In the disclosed embodiment, the predetermined location is within the needle control handle 117, as shown in FIG. 6A, where the luer tubings 43 and 44 terminate at their distal ends and the first and second fluid pathways (arrows A and B) diverge into their relative inner and outer pathways along the catheter. The first and second fluid pathways are isolated from each other by a sealant, for example, polyurethane 135S, provided in the lumen 13L at the predetermined location. As shown in FIGS. 6B, 6C, 6D and 6E, the polyurethane sealant 135S has passages formed therethrough that communicate with the tubings 43 and 44 via their distal ends. The sealant 135S is also formed around at least lead wire 15N for the needle electrode 12, and the tubing 11, for example, a polyimide tubing, that surrounds thermocouple wires 9.

For the second fluid pathway (arrows B), a notch opening 45 is formed in the sidewall of the proximal tubing 13 so that the second fluid pathway extending through the luer tubing 44 traverses the side wall of the proximal tubing 13 and enters the lumen 22L between the guide tubing 22 and the outer surface of the proximal tubing 13. In contrast, the first fluid pathway (arrows A) extends through the lumen of the tubing 43 and continues axially into the coaxial lumen 13L of the proximal tubing 13.

Figure 8:
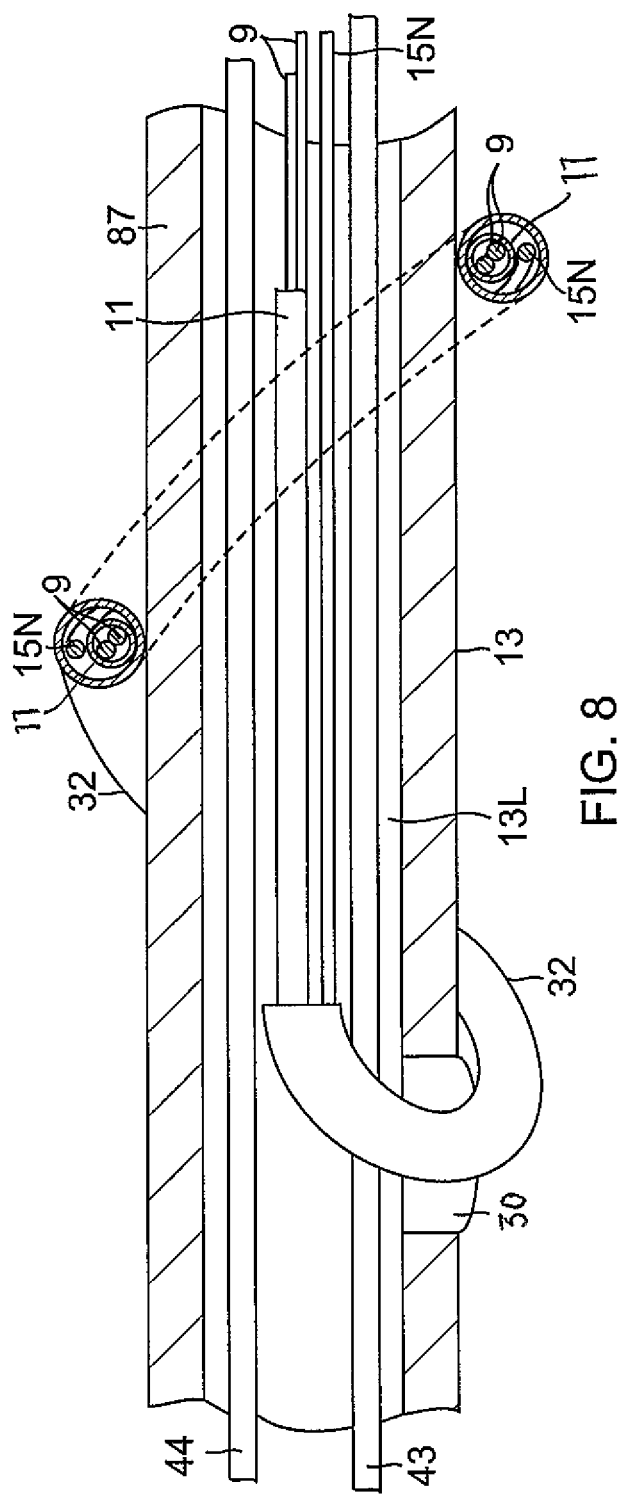
FIG. 8 is a detailed view of the needle injector control handle, including distal portion of a luer connector and fluid supply luer tubings, of section Y of FIG. 6

Because the lead wire 15N, and the thermocouple wires 9 (in their protective tubing 11) extend through the proximal tubing 13, they extend proximally past the deflection control handle 116 and into the injection control handle 117. However, because the interior space of the needle control handle 117 is limited and occupied by the luer connector 86, the lead wire 15N, the thermocouple wires 9 along with the tubing 11 are rerouted (distally) back through the injection control handle 117 and into the deflection control handle 116 where they are connected to the electrical connector 48. As shown in FIG. 6 and in more detail in FIG. 8, these components exit the proximal end of the proximal tubing 13, where these components continue through the rigid tubular portion 87 of the luer connector 86 and then exit through an opening 30 formed in the side wall of the rigid tubular portion 87 toward its proximal end and enter a proximal end of a flexible protective tubing 32 that is coiled in the distal direction around the outer surface of the tubular portion 87 and the protective tubing 97 toward the distal end of the needle control handle 117. The protective tubing 32 passes distally through the distal passage 72 (FIG. 6) and the shaft 70, remaining outside of but alongside the guide tubing 22.

Inside the deflection control handle 116, the lead wire 15N, and the thermocouple wires 9 (along with the lead wires 15T for the tip electrode 2 and the 15R for the ring electrode) are connected to the electrical connector 48 at the proximal end of the deflection control handle 116. As the needle electrode assembly 132 is extended and retracted, the coiled portion of the lead wire 15N and the thermocouple wires 9 in the needle control handle 117 is able to accommodate movement of the proximal tubing 13 without breaking, while advantageously leaving the space-constrained proximal end of the handle 117 for the luer connector 86.

The location of the divergence or the notch opening 45 along the second fluid pathway is selectively positioned so as to be immediately distal to a proximal plunger member 23 so as to minimize the risk of trapping an air bubble. In the disclosed embodiment, the plunger member 23 is a shrink sleeve made of fluorinated ethylene propylene (FEP) and the guide tubing 22 is a made of composite material having an inner layer of polytetrafluoroethylene (PTFE). The plunger member 23 may also be formed, e.g., as a raised ring, as part of the outer surface of the proximal tubing 13. As such, the plunger member 23 forms a fluid-tight proximal end for the second fluid pathway (arrows B) defined by the guide tubing 22 around the needle assembly 132, while allowing the proximal tubing 13 to slide readily and smoothly relative to the guide tubing 22. To fixedly secure the plunger member 23 on the proximal tubing 13, adhesive sealant, such as polyurethane, is applied proximally and distally at 135P and 135D, as illustrated in FIG. 6A.

As shown in FIG. 3A, the catheter includes the biosensor 16 which is used to determine the coordinates of the tip electrode 2, for example, to monitor the precise location of the distal end of the catheter in the patient's body. The biosensor 16 is connected to the cable 16C which extends through the lumen 124 of the tubing 19 of the deflection section 114, and the central lumen 118 of the catheter body 112, and into the deflection control handle 16 where wires of the cable 16C are connected to the circuit board 64. The circuit board amplifies the signals received from the sensor 16 and transmits them to a computer in a form understandable by the computer. The sensor 16 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 77 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, International Publication Nos. WO 95/02995, WO 97/24983, and WO 98/29033, and U.S. patent application Ser. No. 09/882,125 filed Jun. 15, 2001, entitled "Position Sensor Having Core with High Permeability Material," the disclosures of which are incorporated herein by reference.

To use a catheter of the invention, an electrophysiologist may introduce a guiding sheath and dilator into the patient, as is generally known in the art. A guidewire may also be introduced for a catheter adapted for such use. Through the guiding sheath, the entire catheter body 112 can be passed through the patient's vasculature to the desired location. Once the distal end of the guiding sheath reaches the desired location, the catheter can be advanced to expose the deflectable section 114. The thumb control 56 of the control handle 116 may be manipulated as needed to deflect the deflectable section 114 and distal tip section 115 into position. After the distal tip electrode 2 is positioned in contact with tissue, electrical signals in the tissue may be sensed by any combination of the tip electrode 2, the ring electrode 21 and the needle electrode 12, with the signals being transmitted to the electrical connector 48 in the deflection control handle 116 via lead wires 15T, 15R and 15N, for example, to map the region. RF energy may be also applied to the tip electrode 2 and/or the needle electrode 12 via the lead wires 15T and/or 15N to ablate the tissue. In that regard, fluid may be introduced via the second fluid path (arrows B) which passes along the catheter and exits the catheter at the distal end of the tip electrode 2 to cool and displace blood from the area between the proximal exposed area of the needle electrode 12 and the distal face of tip electrode 2.

Additionally, the thumb control 106 of the injector control handle 117 may be depressed distally to extend the needle electrode assembly 132 and deploy the needle electrode 12 for piercing the tissue. RF energy may be applied to the lead wire 15N to energize the needle 55 to ablate the tissue below the surface. In that regard, fluid may be introduced to cool the needle electrode 12. Moreover, the fluid may include saline for irrigation or other types of fluids for diagnostic or therapeutic purposes. The thumb control 106 may be locked in the advanced position by means of the detent feature on the thumb control 106 when the ball 75 is moved distal of the vertical step 78V of the metal end cap 78.

When the thumb control 106 is released by application of a force sufficient to push the ball proximal of the metal end cap 78, the needle electrode 12 retracts into the tip electrode 2 and the catheter distal tip section 115 can be moved and relocated safely within the patient's body.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be adapted to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated catheter body;
   a distal tip section having a tip electrode with a distal end, the tip electrode including a needle centering insert;
   a needle electrode assembly extending through at least the elongated catheter body and the tip electrode, the needle electrode assembly being longitudinally movable relative to the catheter body and distal tip section into an extended position and a retracted position, the needle electrode assembly including a needle electrode;
   an injection control handle proximal of the catheter body configured to move the needle electrode assembly into the extended position and the retracted position;
   a fluid path B extending through at least the catheter body and having a distal exit at the distal end of the tip electrode; and a fluid path A extending through at least the catheter body and having a distal exit at a distal end of the needle electrode assembly, wherein the fluid path B and the fluid path A are isolated from each other, wherein the tip electrode has a longitudinal passage and the needle centering insert is situated in the longitudinal passage, and wherein the fluid path B has a proximal portion that extends through the needle electrode assembly, a distal portion that extends between the needle electrode assembly and a guide tube surrounding the needle electrode assembly, and a mid-portion that connects the proximal portion and the distal portion and traverses a side wall of the needle electrode assembly.

2. The catheter of claim 1, wherein the needle electrode assembly has an elongated proximal tubing extending through the catheter body.

3. The catheter of claim 1, wherein the needle centering insert has a needle passage through which the needle electrode extends.

4. The catheter of claim 3, wherein an inner surface of the needle centering insert lining the needle passage has a cross-section with a smaller diameter and a larger diameter.

5. The catheter of claim 4, wherein portions of the inner surface with the smaller diameter support the needle electrode assembly in the needle passage.

6. The catheter of claim 4, wherein portions of the inner surface with the larger diameter provide axial grooves through the needle passage between the inner surface of the needle centering insert and an outer surface of the needle electrode assembly.

7. The catheter of claim 3, wherein the needle centering insert has a proximal end with at least one indented formation.

8. The catheter of claim 7, wherein the at least one indented formation is configured to provide fluid communication between the fluid path B and at least one axial groove extending between the needle centering insert and the needle electrode assembly.

9. The catheter of claim 1, wherein the mid-portion of the fluid path B is defined by preformed polyurethane.

10. The catheter of claim 1, wherein the guide tube surrounds the needle electrode assembly along its length.

11. The catheter of claim 10,
wherein the distal portion of the fluid path B extends outside of the needle electrode assembly, and
wherein the needle electrode assembly has an outer surface and includes a plunger member on the outer surface proximally of the mid-portion of the fluid path B.

12. The catheter of claim 11, wherein the plunger member comprises a shrink sleeve.

13. A catheter comprising:
an elongated catheter body;
a distal tip section having a tip electrode with a distal end, the tip electrode having a needle channel and a needle centering insert, the needle centering insert having a needle passage and being positioned in the needle channel of the tip electrode;
a needle electrode assembly having a proximal portion extending through at least a lumen in the elongated catheter body and a distal portion extending through the needle passage of the needle centering insert, the needle electrode assembly being longitudinally movable relative to the catheter body and distal tip section into an extended position and a retracted position;
an injection control handle proximal of the catheter body configured to move the needle electrode assembly into the extended position and the retracted position;
a fluid path B extending through at least the catheter body and having a distal exit at the distal end of the tip electrode; and
a fluid path A extending through at least the catheter body and having a distal exit at a distal end of the needle electrode assembly,
wherein the fluid path B and the fluid path A are isolated from each other,
wherein the needle passage has an inner surface with at least one groove configured for fluid flow between the needle centering insert and the distal portion of the needle electrode assembly extending through the needle passage,
wherein the needle centering insert is configured to guide the distal portion of the needle electrode assembly, and
wherein the fluid path B has a proximal portion that extends through the needle electrode assembly, a distal portion that extends between the needle electrode assembly and a guide tube surrounding the needle electrode assembly, and a mid-portion that connects the proximal portion and the distal portion and traverses a side wall of the needle electrode assembly.

14. The catheter of claim 13, wherein the fluid path B communicates with the at least one groove.

15. The catheter of claim 14, wherein the fluid path A passes through the needle electrode assembly.

16. The catheter of claim 14, wherein the proximal portion of the needle electrode assembly includes a proximal tubing and the distal portion of the needle electrode assembly includes a needle electrode, and the fluid path A passes through the proximal tubing and the needle electrode.

* * * * *